US006458928B1

(12) United States Patent
Swanson et al.

(10) Patent No.: US 6,458,928 B1
(45) Date of Patent: Oct. 1, 2002

(54) MICROBIAL SWOLLENIN PROTEIN, DNA SEQUENCES ENCODING SUCH SWOLLENINS AND METHOD OF PRODUCING SUCH SWOLLENINS

(75) Inventors: Barbara A. Swanson; Michael Ward, both of San Francisco, CA (US); Merja Penttilä, Helsinki (FI); Jaakko Pere, Vantaa (FI); Markku Saloheimo, Helsinki (FI)

(73) Assignee: Genecor International, Inc., Palo Alto, CA (US)

( * ) Notice: Subject to any disclaimer, the term of this patent is extended or adjusted under 35 U.S.C. 154(b) by 0 days.

(21) Appl. No.: 09/112,498

(22) Filed: Jul. 9, 1998

Related U.S. Application Data

(63) Continuation-in-part of application No. 08/893,766, filed on Jul. 11, 1997.

(51) Int. Cl.$^7$ .......................... C07K 14/00; A61K 38/00
(52) U.S. Cl. ...................... 530/350; 530/300; 435/262
(58) Field of Search .............................. 530/350, 300; 435/262

(56) References Cited

U.S. PATENT DOCUMENTS

| 5,246,853 A | 9/1993 | Clarkson et al. ............ 435/263 |
| 5,475,101 A | 12/1995 | Ward et al. ............... 536/23.74 |

FOREIGN PATENT DOCUMENTS

| WO | WO 92/06209 | 4/1992 |
| WO | WO 93/05226 | 3/1993 |
| WO | WO 94/26878 | 11/1994 |
| WO | WO 94/28117 | 12/1994 |
| WO | WO 96/35442 | 11/1996 |
| WO | WO 97/14804 | 4/1997 |

OTHER PUBLICATIONS

Bennet & Lasure, ed., *More Gene Manipulations in Fungi*, Academic Press, Inc., p. 70–76, 1991.

Berges, Thierry et al., "Isolation of uridine auxotrophs from *Trichoderma reesei* and efficient transformation with the cloned ura3 and ura5 genes," *Current Genetics*, vol. 19, pp. 359–365, 1991.

Cosgrove, Daniel et al., Autolysis and extension of isolated walls from growing cucumber hypocotyls, *Journal of Experimental Botany*, vol. 45, pp. 1711–1719, 1994.

Fry, Stephen C., "Unzipped by expansins," *Current Biology*, vol. 4, No. 9, pp. 815–817, 1994.

Keller, Elvira et al., "Expansins in growing tomato leaves," *The Plant Journal*, pp. 795–802, 1995.

McQueen–Mason, Simon et al., "Two endogenous proteins that induce cell wall extension in plants," *The Plant Cell*, vol. 4, pp. 1425–1433, 1992.

Sambrook, J. et al., ed. Molecular Cloning: A Laboratory Manual, 2$^{nd}$ ed. *Cold Spring Harbor Laboratory Press*, pp. 1.1–4.54 & 16.1–17.44, 1989.

Shcherban, Tatyana Y. et al., Molecular cloning and sequence analysis of expansins—a highly conserved, multigene family of proteins that mediate cell wall extension in plants, *Proc. Natl., Acad. Sci. USA*, vol. 92, pp. 9245–9249, 1995.

Sheir–Neiss, G. et al., "Characterization of the secreted cellulases of *Trichoderma reesei* wild type and mutants during controlled fermentations," *App. Microbiol. Biotechnol.* vol. 20, pp. 46–53, 1984.

Wang, Ping et al., Production of expansin from light/dark *Trichosanthes kirilowii* var. Japonicum root cultures, *Biotechnology Letters*, vol. 16, No. 9, pp. 955–958, 1994.

Ward, Michael et al., "Use of Aspergillus overproducing mutants, cured for integrated plasmid, to overproduce heterologous proteins,"60 *Appl. Microbiol Biotechnol*, vol. 39, pp. 738–743, 1993.

Zhen–Chang. Li et al., "An oat coleoptile wall protein that induces wall extension in vitro and that is antigenically related to a similar protein from cucumber hypocotyls," *Planta*, vol. 191, pp. 349–356, 1993.

Primary Examiner—Karen Cochrane Carlson
Assistant Examiner—Rita Mitra
(74) Attorney, Agent, or Firm—Genencor International, Inc.

(57) ABSTRACT

A novel microbial protein is described which appears to have significant homology to plant expansin proteins and has the ability to weaken filter paper and swell cellulose. A DNA is described which encodes the novel protein.

6 Claims, 7 Drawing Sheets

GGCACGAGGAACTGTTAGACGGGATGGCTGGTAAGCTTATCCTCGTGGCTCTAGCAAGCCTTGTATCACTCTCTATTCAGCAGAATTGCG 90

|————— signal sequence —————|
                  M  A  G  K  L  I  L  V  A  L  A  S  L  V  S  L  S  I  Q  Q  N  C CAGCATTATTTGGCCAATGTGGAGGCATAGGGTGGTCCGGCACCACAGTTGCGTTGCTGGCGCCAGTGCAGTTTTGTCAATGACTGGT 180
                                                |————— CBD
A  A  L  F  G  Q  C  G  G  I  G  W  S  G  T  T  C  C  V  A  G  A  Q  C  S  F  V  N  D  W ACTCCCAGTGCCTTGCGTCGTCTTCACCCGGCGGAACTGGCAGTTGCTTCCTCTAGCTTGTTTCACGGACGTCAGCATCCTCAT 270
Y  S  Q  C  L  A  S  T  G  G  N  P  P  N  G  T  S  S  S  L  V  S  R  T  S  S  A  S  S
—— CBD ——|

CCGTCGGCTCGTCTTCACCCGGCGTCTTCACCACAGATACAGTTACCGTGGCTCCTCATT 360
S  V  G  S  S  S  P  G  G  N  S  P  T  G  S  A  S  T  Y  T  T  T  D  T  A  T  V  A  P  H

CGCAGTCTCCTTACCCGCATTGCCGGCATCCAGTGCGTGGACCCTCGTGGATAATGTTGCTGCCCATCATATTGTGCTAATG 450
S  Q  S  P  Y  P  S  I  A  A  S  C  G  S  W  T  L  V  D  N  V  C  C  P  S  Y  C  A  N

ATGACACAATCCGAGTCGTGCATGCTCAGGCTGCCGTACCTGCACTGCAGTAGATCAACGAGCCCACTTTGGCCTAACGAGCGGCGCGGGAACCATGTATCCAGAGGTCC 540
M  D  T  S  E  S  C  G  T  C  T  T  P  P  S  A  D  C  K  S  G  T  M  Y  P  E  V

ATCACGTATCCAGCAACGAGAGCTGGCACTACAGCCAGTGTTACAGCGGATCCGATGCTGGCCGTGTGACGCTTTTTGTACAGCGTATCCCCTGC 630
I  T  Y  P  Q  Q  R  E  L  A  L  Q  P  V  L  Q  R  I  R  C  W  P  C  D  G  L  L  V  Q  R  I  P  C
H  H  V  S  S  N  E  S  W  H  Y  S  R  S  T  H  F  G  L  T  S  G  G  A  C  G  F  G  L  Y

GTCTCTGCACAAAGGGCAGTGTTACAGCCAGTGGATCCAAACTTCGTGTGCAACTTCGGCAGCTCCCAAACGGCGATTACTACACCCCAATTCTGGTCCTCGTTGCCAG 720
G  L  C  T  K  G  S  V  T  A  S  W  T  D  P  M  L  G  A  T  C  D  A  F  C  T  A  Y  P  L

TTTGCAAAGACCCTCGGCACTACCCTTCGTGTGCAACTTCGCAATTCGTGGCAACTTCGCCCCAAAACGGCGATTACTACACACCCCAATTCTGGTCCTCGTTGCCAG 810
L  C  K  D  P  T  G  T  T  L  R  G  N  F  A  A  P  N  G  D  Y  Y  T  Q  F  W  S  S  L  P

GAGCCCTCGATAACTACCTGTCCTGCGGCGAGTGCATTGAGCTGATACAAAACAAAGCCCGATGGACCGATTATGCTGTCGGAGAAGCCG 900
G  A  L  D  N  Y  L  S  C  G  E  C  I  E  L  I  Q  T  K  P  D  G  T  D  Y  A  V  G  E  A

FIG._1A

```
GCTACACGGATCCAATTACTCTCGAGATTGTGGACAGTCGTGCCCGTGCAGCGCGAACTCCAAGTGGTGCTGTGTCCGGGCGCCGATCATT  990
 G  Y  T  D  P  I  T  L  E  I  V  D  S  C  P  C  S  A  N  S  K  W  C  C  G  P  G  A  D  H

GCGGAGAGATCGACTTCAAATACGGCTGTCCTCTTCCTGCTGACAGCATTCATCTCGACCTGTCAGACATTGCCATGGGCCGTTTGCAGG 1080
 G  E  I  D  F  K  Y  G  C  P  L  P  A  D  S  I  H  L  D  L  S  D  I  A  M  G  R  L  Q

GCAATGGATCACTAACCAATGGCGTCATCCCGACTCGATATAGAAGAGTCCAAAGTTGGGAACGCCTACATTTGGCTTCGAA 1170
 C  N  G  S  L  T  N  G  V  I  P  T  R  Y  R  R  V  Q  C  P  K  V  G  N  A  Y  I  W  L  R

ATGGCGGAGGGCCTTACTATTTTGCTCTCACGGCAGTCAACACCGGGCTCAGTCAGTCACCAAAATCGAGATCAAGGGCGCAGACA 1260
 N  G  G  P  Y  Y  F  A  L  T  A  V  N  T  N  G  P  G  S  V  T  K  I  E  I  K  G  A  D

CCGACAACTGGGTTGCCCTTGGTCCATGACCCCAAACTATACGAGTAGCCGCCAAGAACGCTATGGCAGTTGGGTAATCCCACAGGGAT 1350
 T  D  N  W  V  A  L  V  H  D  P  N  Y  T  S  S  R  P  Q  E  R  Y  G  S  W  V  I  P  Q  G

CAGGGCCCCTTTAACTTGCCTGTCGGAATTCGTCGACTAGCCCAACGGGGAACAGATTGTGAATGAACAGGCCATCAAGACATTCACTC 1440
 S  G  P  F  N  L  P  V  G  I  R  L  T  S  P  T  G  E  Q  I  V  N  E  Q  A  I  K  T  F  T

CTCCGGCCACAGGTGACCCCAATTTTACTACAATTTTACTACAATTGACATTGGTGTGCAGTTTAGCCAGAATTGATGGCAAGCATTGGGCAATGGGCTTC 1530
 P  P  A  T  G  D  P  N  F  Y  Y  I  D  I  G  V  Q  F  S  D  N  .  W  Q  A  L  G  N  G

TTGCTGTGGGACAATGATTAGGCTAGATTCTCAAGTATGTGGTGTACGTCTTCGTGTGTATAGATAGGTATGCTGTTCACT 1620
TAAATACACATCCTTTGGTACGTTG 1645
```

FIG.\_1B

```
VHHVSSNESWHYSRSTHFGL- - - - -TSGGACGFGLYGLCT  T.r. swoll.
G- - - - - - -GWQSAHATFYGGGDASGTMGGACGYG- -NLYS  Plant exp. cons.

KGSVTASWTDPMLGATCDAFCTAYPLLCKDPTGTTLRGNF    T.r. swoll.
QGYGTNT- - - - - - - - - - - - - - - - - - - - - - - - -   Plant exp. cons.

AAPNGDYYTQFWSSLPGAL-DNYLSCGECIELIQTKPDGT    T.r. swoll.
- - - -AALSTALFNNGLSCGACFELT- - - - - - - -    Plant exp. cons.

DYAVGEAGYTDPIT

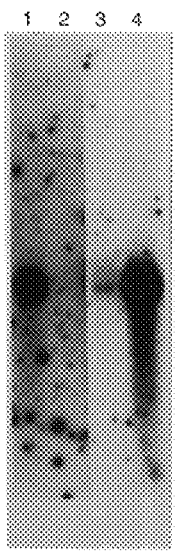
FIG._3
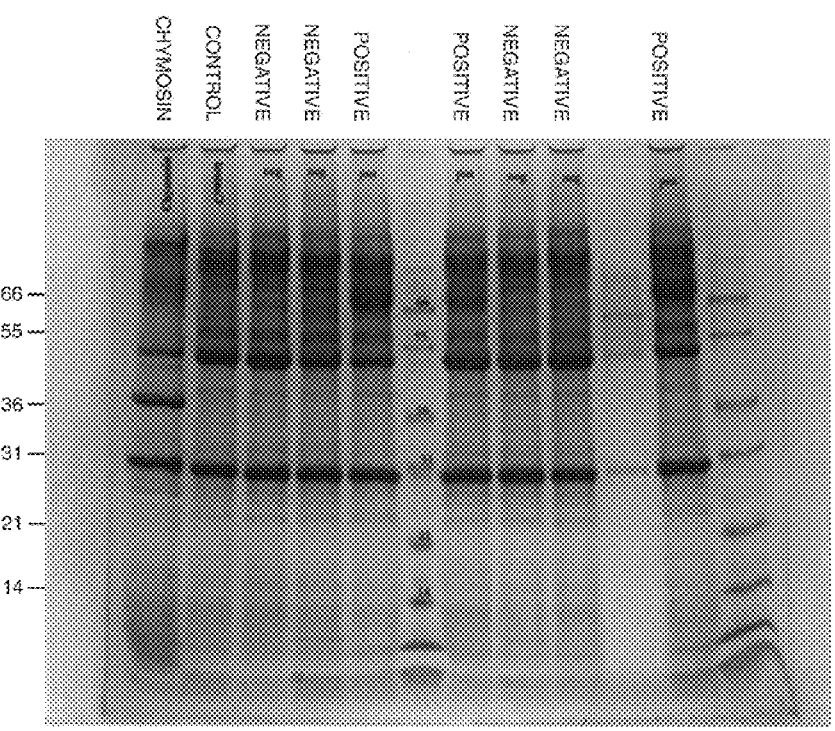
FIG._6

```
                   0         10        20        30        40        50        60        70
                   |.........|.........|.........|.........|.........|.........|.........|
consen.                     .........D..|...C....|..........|..C...C....C....D..WC|
                                                            |.C.C....C....D-n-DPkWC1
                                                            |.C.C....C...D..WC|
CuExS1            dyGGWqsAHATFYGGgDASGTMGGACGYGNLYSQGYGtNTVALSTALFNnGlSCGACFEMtC-tn-DPkWC1
CuExS2           ftaSGWapAHATFYGesDASGTMGGACGYGNLYQTGYGtrTAALSTALFNdGaSCGqCFKIiCdyktDPrWCi
AtEx1      nsardvngyagGGWvnAHATFYGGgDASGTMGGACGYGNLYSQGYGtNTAALSTALFNnGlSCGACFEIrCq-n-DGkWC1
AtEx2           insddnGGWerGHATFYGGaDASGTMGGaCGYGNLHSQGYGl0TAALSTALFNsGqkCGACFELqCe-d-DPeWCi
AtEx5      gyrrgghhpgghmGpWinAHATFYGGghDASGTMGGACGYGNLYSQGYGleTAALSTALFDqGlSCGACFELmCv-n-DPqWCi
AtEx6         lseairipgvyngGGWetAHATFYGGsDASGTMGGACGYGNLYSQGYGvNTAALSTALFNnGfSCGACFELkC-as-DPkWCh
RiEx

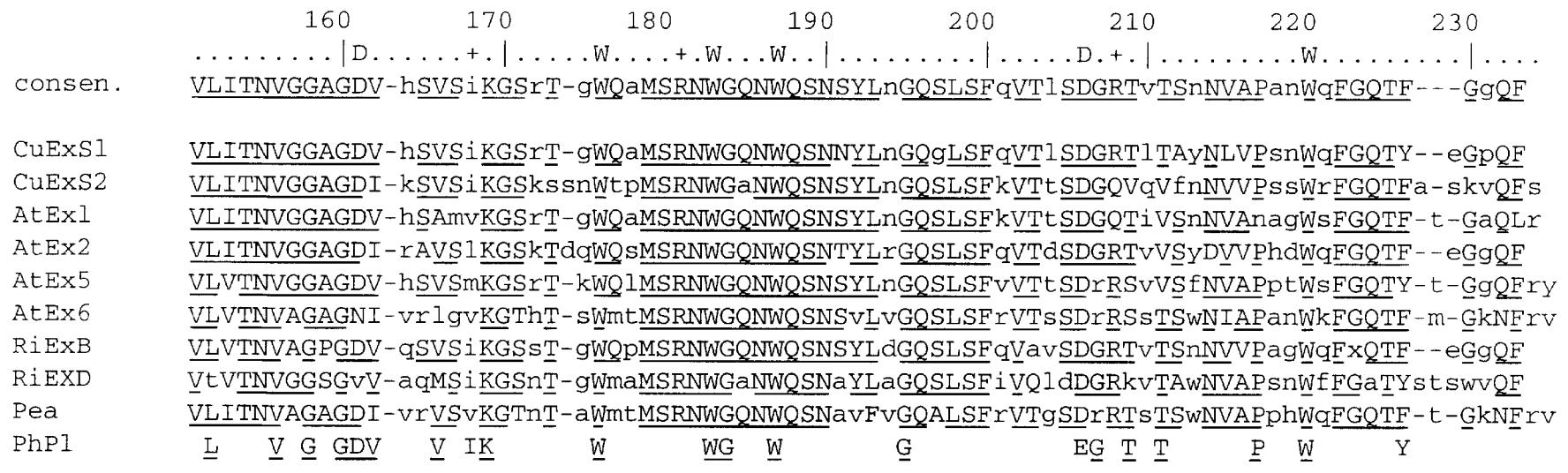

FIG._4B

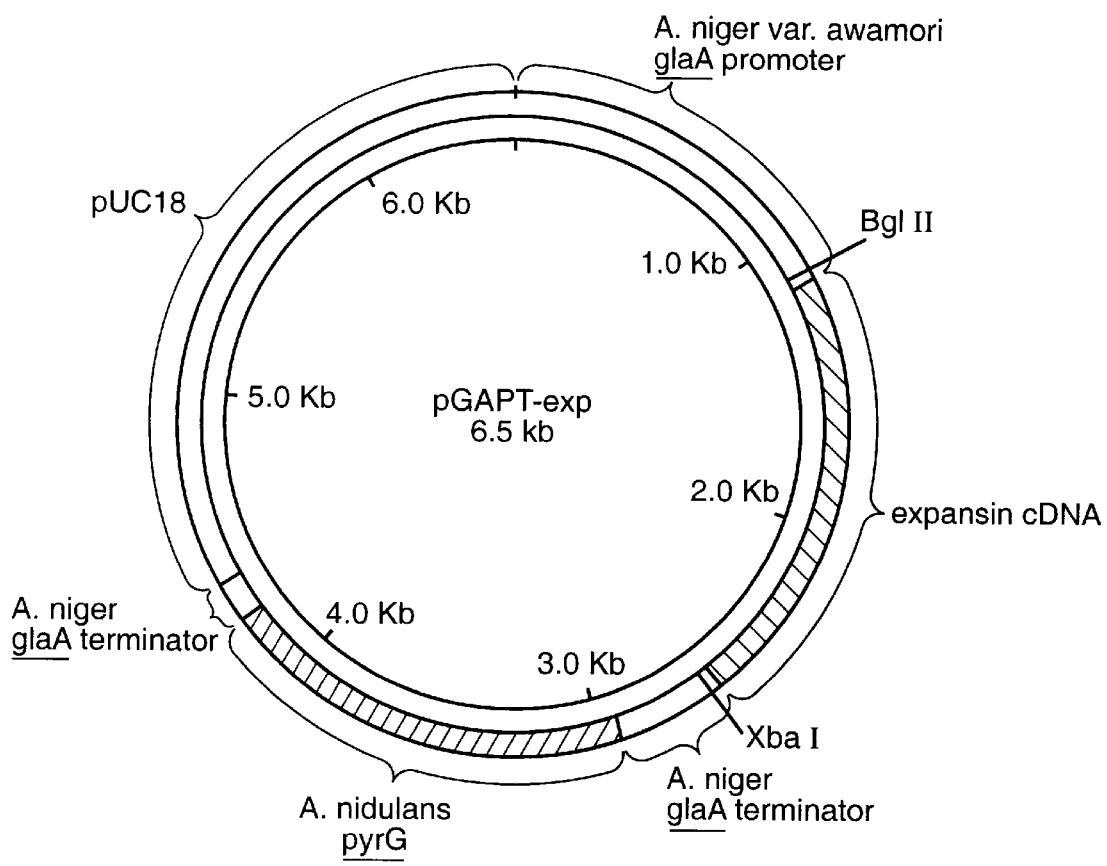
FIG._5

MICROBIAL SWOLLENIN PROTEIN, DNA SEQUENCES ENCODING SUCH SWOLLENINS AND METHOD OF PRODUCING SUCH SWOLLENINS

CROSS-REFERENCE TO RELATED APPLICATIONS

This application is a continuation-in-part of U.S. application Ser. No. 08/893,766, filed Jul. 11, 1997 and which is incorporated herein by reference in its entirety.

BACKGROUND OF THE INVENTION

Osmotic uptake of water is the driving force of plant cell expansion. As water enters the cell, the protoplast expands but is restrained by the cell wall. Moreover, a rigid complex of cellulose microfibril polymers embedded in a glue-like matrix of pectins, hemicelluloses and proteins forms part of this wall in mature cells. It has long been thought that some "wall loosening" factor must be present which alters immature cell wall mechanical properties and allows it to undergo a process of elongation. McQueen-Mason et al., *Plant Cell*, Vol. 4, pp. 1425–1433 (1992) studied plant cell enlargement regulation by employing a reconstitution approach. The authors found that a crude protein extract from the cell walls of growing cucumber seedlings possess the ability to induce the extension of isolated cell walls. Sequential HPLC fractionation of the active wall extract revealed two proteins with molecular masses of 29 and 30 kD associated with the activity. Each protein, by itself, could induce wall extension without detectable hydrolytic breakdown of the wall and appeared to mediate "acid growth" responses of isolated walls and may catalyze plant cell wall extension by a novel biochemical mechanism.

Shcherban et al., *Proc. Nat. Acad. Sci.*, USA, Vol. 92, pp. 9245–9249 (1995) isolated cDNA's encoding these two cucumber proteins and compared them to anonymous expressed sequence tags from various sources. Rice and Arabidopsis expansin cDNA were identified from these collections and showed at least four different expansin cDNA's in rice and six different expansin cDNA's in Arabidopsis. The authors concluded that expansin are highly conserved in size and sequence (60–87% amino acid identity and 75–95% similarity between any pairwise comparison) and that the multigene family formed before the evolutionary divergence between monocotyledons and dicotyledons. Shcherban et al. states that the high conservation of this mutligene family indicates that the mechanism by which expansin promotes cell wall extension tolerates little variation in protein structure.

Wang et al., *Biotech. Lett.*, Vol. 16, No. 9, pp. 955–958 (1994) discovered two proteins in a Chinese medicinal cucumber, *Trichosanthes kirilowii*, which appear to be similar to the S1 and S2 proteins which demonstrate cell wall extension properties. Similar proteins were also found in growing tomato leaves (Keller et al., *The Plant Journal*, Vol. 8, No. 6, pp. 795–802 (1995)) and in oat coleoptile walls (Li et al., *Planta*, Vol. 191, pp. 349–356 (1993)).

Cosgrove et al., *J. Exp. Botany*, Vol. 45, Special Issue, pp. 1711–1719 (1994) suggested that cooperative interactions between the expansin proteins and pectinases and cellulases may occur, wherein the enzymes modify the matrix so that other wall extension mechanisms may be more effective. Fry, *Current Biology*, Vol. 4, No. 9 (1994) suggest that, in loosening cell walls, expansin seems unlikely to break cellulose-cellulose bonds as microfibrils remain intact during growth. Thus, the authors discount the observed breakage of hydrogen bonds in filter paper as a side issue and suggest that expansin may lengthen inter-microfibrillar tethers by causing hemicellulose chains to detach from cellulose microfibrils to allow extension.

Despite the pioneering work previously done in the area of cell wall extension and its causes, work related to the usefulness and operability of expansins is still in its infancy. Moreover, the sources of expansin up to now have been exclusively from plant origins, for which expression systems may not be optimal for large scale production. Accordingly, it would be valuable to have a ready source of expansin-like material which is capable of being produce in large quantities from organisms which are established high output producers of biological materials, such as fungi, bacteria or other well characterized microorganisms.

SUMMARY OF THE INVENTION

It is an object of the present invention to provide for a swollenin protein which is derived from a microbial non-plant source.

It is another object of the present invention to provide for a swollenin protein which is expressible in a well-characterized microorganism, for example a fungus or bacteria, so as to facilitate its production in large quantities.

It is yet another object of the present invention to provide a DNA sequence corresponding to a microbial swollenin which can be used in industrial production of swollenin protein.

It is yet another object of the present invention to provide for novel and useful methods of altering cellulosic substrates, such as pulp and paper, cellulose based textile fibers, animal feed and corn wet milling or dry milling polysaccharide waste products or other cellulosic biomass.

According to the present invention, a partially or wholly isolated swollenin protein derived from a fungus or bacteria is provided. Preferably, the swollenin is derived from a filamentous fungus, more preferably, from a filamentous fungus such as Trichoderma spp., Humicola spp., Neurospora spp., Aspergillus spp., Fusarium spp., Penicillium spp., or Gliocladium spp. and most preferably, from Trichoderma spp. In a particularly preferred embodiment of the present invention, the swollenin comprises a sequence according to SEQ. ID NO:2, has at least 70% sequence identity with the sequence provided in SEQ. ID NO:2 or comprises a derivative of the sequence according to SEQ. ID NO:2, wherein the swollenin further has the ability to weaken filter paper and/or swell cotton fibers.

In another embodiment of the present invention, a DNA is provided encoding a swollenin protein from a fungus or bacteria. Preferably, the DNA is derived from a filamentous fungus such as Trichoderma spp., Humicola spp., Neurospora spp., Aspergillus spp., Fusarium spp., Penicillium spp., or Gliocladium spp. Also preferably, the DNA comprises the sequence according to SEQ. ID. NO:1. Alternately, the DNA has at least 70% sequence identity with the sequence according to SEQ. ID NO:1 or comprises a derivative of the sequence according to SEQ. ID NO:1, wherein said DNA encodes a swollenin protein which has the ability to weaken filter paper and/or swell cotton fibers. In a preferred embodiment of the invention, the DNA hybridizes with a DNA having all or part of the sequence provided in SEQ ID NO:1.

In another embodiment of the invention, a DNA is provided which encodes a microbial, e.g., bacterial or fungal, swollenin, and the DNA hybridizes with a DNA probe encoding a peptide having an amino acid sequence comprising SEQ. ID NO:14, SEQ. ID NO:15, SEQ. ID NO:16, SEQ. ID NO:17 or SEQ. ID NO:18. Vectors comprising such DNA, host cells having been transformed with such vectors and fermentation broths produced by such transformed host cells are also within the scope of the present invention.

In yet another embodiment of the present invention, a method of producing swollenin protein is provided comprising the steps of (a) obtaining a host cell which has been transformed with a vector comprising DNA encoding a swollenin protein, the DNA being isolated from a fungus or bacteria; (b) culturing the host cell under conditions suitable for the expression and, optionally, secretion, of the swollenin protein; and (c) recovering the fermentation broth containing said swollenin protein.

Since fungi and bacteria do not generally have a cellulosic cell wall and in any event are not known to increase in size by the same mechanism as higher plants, Applicants discovery that these microorganisms produce proteins having expansin-like properties is not suggested by previous work related to plant expansins. Thus, the finding that the cellulolytic fungus Trichoderma spp. produces an expansin-like protein is unexpected. However, it is apparent that the microbial class of proteins differs from those heretofore discovered in plants. For example, the presence of a region on the microbial swollenin protein described herein corresponding to the cellulose binding domain of fungal cellulolytic enzymes suggests that this protein is secreted to act in concert with the naturally secreted cellulases and hemicellulases in order to facilitate hydrolysis of cellulosic biomass in the environment. Consistent with this suggestion, the *Trichoderma reesei* swollenin gene was found to be expressed when the fungus was grown on cellulose as a sole carbon source, but not when the carbon source for growth was glucose. This pattern of regulation of gene expression is similar to that observed for many of the Trichoderma cellulose and hemicellulose genes. These unexpected findings lead to the conclusion that cellulose or hemicellulose degrading micro-organisms, including bacteria, yeast and fungi, would also produce such swollenin proteins.

Accordingly, it is an advantage of the present invention that the swollenins provided herein may have utility in many applications for which cellulase is currently used, for example, cleaning textiles (laundry detergents and pre-wash compositions), modifying textiles (depilling, color restoration, anti-greying), stonewashing denim, biomass conversion to glucose, and improvement of the nutritive value of animal feeds. Similarly, it is contemplated that an advantage of the present invention is that swollenins may have a synergistic or additive effect in combination with other enzymes, particularly cellulases such as endoglucanases. In other cases, it is possible that swollenins would have a deleterious effect in an application; for example, they may cause excessive fabric strength loss when present as a side activity in an endoglucanase produced by fermentation of a microorganism and used for fabric cleaning or modification. In such a case, removal of the swollenin from a cellulase product may be beneficial and may be accomplished by biochemically removing the product from the resultant cellulase mixture, through genetic engineering to prevent its expression or to inactivate the gene or by adding a chemical inhibitor to the composition comprising the swollenin.

BRIEF DESCRIPTION OF THE DRAWINGS

FIGS. 1A–1B illustrate the nudeotide sequence (SEQ ID NO:1) and predicted corresponding amino acid sequence (SEQ ID NO:2) of a cDNA clone obtained from a *Tinchoderma reesei (longibrachiatum)* RNA after growth on a mixed carbon source.

FIG. 2 illustrates a comparison of the consensus amino acid sequence for plant expansin proteins (SEQ ID NO:3) and the sequence of the swollenin (SEQ ID NO:4) described herein showing the regions of amino acid homology.

FIG. 3 illustrates the result of Northern blotting of RNA samples prepared from *Trichoderma reesei (longibrachiatum)* mycelium grown on different carbon sources and probed with swollenin cDNA. Lane 1: cellulose; lane 2: glucose; lane 3: sorbitol; lane 4: sorbitol culture induced by sophorose.

FIGS. 4A–4B illustrates a comparison of nine known plant expansin amino acid sequences (SEQ ID NOS:5–13) showing the extensive homology present in plant expansins.

FIG. 5 shows the plasmid map for pGAPT-exp.

FIG. 6 illustrates the results of an SDS-PAGE gel run with culture supernatants and controls. Aspergillus transformants which were producing the *T. reesei* swollenin have a band running above the 66 kD marker band and this band is missing from lanes of the negative control (Aspergillus strain before the transformation).

DETAILED DESCRIPTION OF THE INVENTION

Definitions

"Swollenin" means a protein or polypeptide or domain of a protein or polypeptide of microbial, i.e., fungal or bacterial, origin which has the ability to facilitate weakening of filter paper and the swelling of cotton fibers without having cellulolytic activity, i.e., catalytic activity involving the breakage of individual cellulose strands into smaller monomer (glucose) or oligomers (polysaccharides). While it is useful to define swollenins loosely in terms of the expansin proteins described in McQueen-Mason et al., *Plant Cell*, Vol. 4, pp. 1425–1433 (1992), it is also apparent that microbial swollenins have distinct properties, for example, microbial swollenins are much larger proteins than plant expansins and have a low level of sequence identity with plant expansins. Moreover, certain microbial swollenin proteins exist in conjunction with a cellulose binding domain and may further exist in conjunction with a catalytic cellulase domain. For example, the swollenin protein derived from *Trichoderma reesei* shown herein possesses a cellulose binding domain.

It is contemplated herein that swollenins may be derived from microbial origins, and particularly from fungal or bacterial origins. Specifically, it is contemplated that microorganisms which possess cellulolytic capabilities will be excellent sources of swollenin protein. In a particularly preferred embodiment of the invention, the swollenin is derived from Trichoderma spp., particularly *Trichoderma reesei (longibrachiatum)*. However, also preferably, the swollenin and/or DNA encoding swollenin according to the present invention is derived from a fungus, such as, Absidia spp.; Acremonium spp.; Agaricus spp.; Anaeromyces spp.; Aspergillus spp., including *A. auculeatus, A. awamori, A. flavus, A. foetidus, A. fumaricus, A. fumigatus, A. nidulans, A. niger, A. oryzae, A. terreus* and *A. versicolor*; Aeurobasidium spp.; Cephalosporum spp.; Chaetomium spp.; Coprinus spp.; Dactyllum spp.; Fusarium spp., including *F. conglomerans, F. decemcellulare, F. javanicum, F. lini, F.oxysporum* and *F. solani*; Gliocladium spp.; Humicola spp., including *H. insolens* and *H. lanuginosa*; Mucor spp.; Neurospora spp., including *N. crassa* and *N. sitophila*; Neocallimastix spp.; Orpinomyces spp.; Penicillium spp;

Phanerochaete spp.; Phlebia spp.; Piromyces spp.; Pseudomonas spp.; Rhizopus spp.; Schizophyllum spp.; Trametes spp.; Trichoderma spp., including *T reesei, T. reesei (longibrachiatum)* and *T. viride*; and Zygorhynchus spp. Similarly, it is envisioned that a swollenin and/or DNA encoding a swollenin as described herein may be found in cellulolytic bacteria such as Bacillus spp.; Cellulomonas spp.; Closttidium spp.; Myceliophthora spp.; Thermomonospora spp.; Streptomyces spp., including *S. olivochromogenes*; specifically fiber degrading ruminal bacteria such as *Firobacter succihogenes*; and in yeast including *Candida torresii; C. parapsllosis; C. sake; C. zeylanoides; Pichia minuta; Rhodotorula glutinis; R. mucilaginosa;* and *Sporobolomyces holsaticus.*

Preferably, swollenin proteins according to the present invention are isolated or purified. By purification or isolation is meant that the swollenin protein is altered from its natural state by virtue of separating the swollenin from some or all of the naturally occurring constituents with which it is associated in nature. This may be accomplished by art recognized separation techniques such as ion exchange chromatography, affinity chromatography, hydrophobic separation, dialysis, protease treatment, ammonium sulphate precipitation or other protein salt precipitation, centrifugation, size exclusion chromatography, filtration, microfiltration, gel electrophoresis or separation an a gradient to remove whole cells, cell debris, impurities, extraneous proteins, or enzymes undesired in the final composition. It is further possible to then add constituents to the swollenin containing composition which provide additional benefits, for example, activating agents, anti-inhibition agents, desirable ions, compounds to control pH or other enzymes such as cellulase.

Hybridization is used herein to analyze whether a given fragment or gene corresponds to the swollenin described herein and thus falls within the scope of the present invention. The hybridization assay is essentially as follows: Genomic DNA from a particular target source is fragmented by digestion with a restriction enzyme(s), e.g., EcoR I, Hind III, Bam Hl, Cla I, Kpn I, Mlu I, Spe I, Bgl II, Nco I, Xba I, Xho I and Xma I (supplied by New England Biolabs, Inc., Beverly, Mass. and Boehringer Mannheim) according to the manufacturer's instructions. The samples are then electrophoresed through an agarose gel (such as, for example, 0.7% agarose) so that separation of DNA fragments can be visualized by size. The gel may be briefly rinsed in distilled $H_2O$ and subsequently depurinated in an appropriate solution (such as, for example, 0.25 M HCl) with gentle shaking followed by denaturation for 30 minutes (in, for example, 0.4 M NaOH). A renaturation step may be included in which the gel is placed in 1.5 M NaCl, IM Tris, pH 7.0 with gentle shaking for 30 minutes. The DNA should then be transferred onto an appropriate positively charged membrane, for example the Maximum Strength Nytran Plus membrane (Schleicher & Schuell, Keene, N. H.), using a transfer solution (such as, for example, 6×SSC (900 mM NaCl, 90 mM trisodium citrate). After the transfer is complete, generally at about 2 hours or greater, the membrane is rinsed and air dried at room temperature after using a rinse solution (such as, for example, 2×SSC[2×SSC=300 mM NaCl, 30 mM trisodium citrate]). The DNA should then be crosslinked to the membrane by either UV-crosslinking or by baking in an oven using temperatures recommended by the membrane manufacturer. The membrane should then be prehybridized, (for approximately 2 hours or more) in a suitable prehybridization solution (such as, for example, an aqueous solution containing per 100 mls: 30–50 mls formamide, 25 mls of 20×SSPE (1×SSPE=0.18 M NaCl, 1 mM EDTA, 10 mM $NaH_2PO_4$, pH 7.7), 2.5 mls of 20% SDS, 1 ml of 10 mg/ml sheared herring sperm DNA).

A DNA probe taken from the sequence in FIGS. 1A–1B should be isolated by electrophoresis in an agarose gel, the fragment excised from the gel and recovered from the excised agarose. This purified fragment of DNA is then labeled (using, for example, the Megaprime labeling system according to the instructions of the manufacturer to incorporate $p^{32}$ in the DNA (Amersham International plc, Buckinghamshire, England)). The labeled probe is denatured by heating to 95° C. for 5 minutes and immediately added to the prehybridization solution above containing the membrane. The hybridization reaction should proceed for an appropriate time and under appropriate conditions, for example, for 18 hours at 37° C. with gentle shaking. The membrane is rinsed (for example, in 2×SSC/0.3% SDS) and then washed with an appropriate wash solution and with gentle agitation. The stringency desired will be a reflection of the conditions under which the membrane (filter) is washed. [1] Eesto Corp. v. Shokersu Kogyo Kabushiki Co., No. 95–1066, 2000 WL 1753646 (Fed Cir. Nov. 29, 2000).

Specifically, the stringency of a given reaction (i.e., the degree of homology necessary for successful hybridization) will depend on the washing conditions to which the filter from the Southern Blot is subjected after hybridization. "Low-stringency" conditions as defined herein will comprise washing a filter from a Southern Blot with a solution of 0.2×SSC/0.1% SDS at 20° C. for 15 minutes. "Standard-stringency" conditions comprise a further washing step comprising washing the filter from the Southern Blot a second time with a solution of 0.2×SSC/0.1% SDS at 37° C. for 30 minutes.

"Cellulase" is a well classified category of enzymes in the art and includes enzymes capable of hydrolyzing cellulose polymers to shorter oligomers and/or glucose. Common examples of cellulase enzymes include exo-cellobiohydrolases and endoglucanases and are obtainable from many species of cellulolytic organisms, particularly including fungi and bacteria.

"Hemicellulase" is also a well classified category of enzymes in the art and includes enzyme capable of hydrolyzing hemicellulose polymers to shorter oligomers. Common examples of hemicellulases include xylanase and mannanase.

"Cellulose containing materials" means materials comprising cellulose polymer as one of its constituents. Cellulose will thus include sewn or unsewn fabrics or other articles made of pure cotton or cotton blends including cotton woven fabrics, cotton knits, cotton denims, cotton yarns and the like or blends thereof including one or more non-cotton fibers including synthetic fibers such as polyamide fibers (for example, nylon 6 and nylon 66), acrylic fibers (for example, polyacrylonitrile fibers), and polyester fibers (for example, polyethylene terephthalate), polyvinyl alcohol fibers (for example, Vinylon), polyvinyl chloride fibers, polyvinylidene chloride fibers, polyurethane fibers, polyurea fibers and aramid fibers. "Cellulose" further means any cotton or non-cotton containing cellulosic fabric or cotton or non-cotton containing cellulose blend including natural cellulosics and manmade cellulosics (such as jute, flax, ramie, rayon, TENCEL®). Included under the heading of manmade cellulosics are regenerated fabrics that are well known in the art such as rayon. Other manmade cellulosics include chemically modified cellulose fibers (e.g, cellulose derivatized by acetate) and solvent-spun cellulose fibers. Of course, included within the definition of cellulose containing fabric is any garment or yarn made of such materials. Similarly, "cellulose containing fabric" includes textile fibers made of such materials. Additionally, materials comprising cellulose include wood, wood pulp and other plant-based fiber (i.e., grasses, feeds, seeds, trees, corn husks), paper, cardboard, particle board, nutritional fiber and non-nutritional fiber.

"Derivative" means a protein which is derived from a precursor protein (e.g., the native protein) by addition of one or more amino acids to either or both the C- and N-terminal end, substitution of one or more amino acids at one or a number of different sites in the amino acid sequence, deletion of one or more amino acids at either or both ends of the protein or at one or more sites in the amino acid sequence, or insertion of one or more amino acids at one or more sites in the amino acid sequence. The preparation of a swollenin derivative is preferably achieved by modifying a DNA sequence which encodes for the native protein, transformation of that DNA sequence into a suitable host, and expression of the modified DNA sequence to form the derivative swollenin. The derivative of the invention includes peptides comprising altered amino acid sequences in comparison with a precursor amino acid sequence (e.g., a wild type or native state swollenin), which peptides retain a characteristic swollenin nature of the precursor swollenin but which have altered properties in some specific aspect. For example, a swollenin derivative may have an increased pH optimum or increased temperature or oxidative stability but will retain its characteristic cellulose modification activity. Similarly, derivatives according to the present invention include a cellulose binding domain which has either been added, removed or modified in such a way so as to significantly impair or enhance its cellulose binding ability. Similarly, a catalytic cellulolytic domain may either be added, removed or modified to operate in conjunction with the swollenin. It is contemplated that derivatives according to the present invention may be derived from a DNA fragment encoding a swollenin derivative wherein the functional activity of the expressed swollenin derivative is retained. Derivative further includes chemical modification to change the characteristics of the swollenin.

"Expression vector" means a DNA construct comprising a DNA sequence which is operably linked to a suitable control sequence capable of effecting the expression of the DNA in a suitable host. Such control sequences may include a promoter to effect transcription, an optional operator sequence to control transcription, a sequence encoding suitable ribosome-binding sites on the mRNA, and sequences which control termination of transcription and translation. Different cell types are preferably used with different expression vectors. A preferred promoter for vectors used in *Bacillus subtilis* is the AprE promoter; a preferred promoter used in *E. coli* is the Lac promoter, a preferred promoter used in *Saccharomyces cerevisiae* is PGK1, a preferred promoter used in *Aspergillus niger* is glaA, and a preferred promoter for *Trichoderma reesei* (*longibrachiatum*) is cbhI. The vector may be a plasmid, a phage particle, or simply a potential genomic insert. Once transformed into a suitable host, the vector may replicate and function independently of the host genome, or may, under suitable conditions, integrate into the genome itself. In the present specification, plasmid and vector are sometimes used interchangeably. However, the invention is intended to include other forms of expression vectors which serve equivalent functions and which are, or become, known in the art. Thus, a wide variety of host/expression vector combinations may be employed in expressing the DNA sequences of this invention. Useful expression vectors, for example, may consist of segments of chromosomal, non-chromosomal and synthetic DNA sequences such as various known derivatives of SV40 and known bacterial plasmids, e.g., plasmids from *E. coli* including col E1, pCR1, pBR322, pMb9, pUC 19 and their derivatives, wider host range plasmids, e.g., RP4, phage DNAs e.g., the numerous derivatives of phage λ, e.g., NM989, and other DNA phages, e.g., M13 and filamentous single stranded DNA phages, yeast plasmids such as the 2μ plasmid or derivatives thereof, vectors useful in eukaryotic cells, such as vectors useful in animal cells and vectors derived from combinations of plasmids and phage DNAs, such as plasmids which have been modified to employ phage DNA or other expression control sequences. Expression techniques using the expression vectors of the present invention are known in the art and are described generally in, for example, Sambrook et al., *Molecular Cloning: A Laboratory Manual, Second Edition*, Cold Spring Harbor Press (1989). Often, such expression vectors including the DNA sequences of the invention are transformed into a unicellular host by direct insertion into the genome of a particular species through an integration event (see e.g., Bennett & Lasure, *More Gene Manipulations in Fungi*, Academic Press, San Diego, pp. 70–76 (1991) and articles cited therein describing targeted genomic insertion in fungal hosts, incorporated herein by reference).

"Host strain" or "host cell" means a suitable host for an expression vector comprising DNA according to the present invention. Host cells useful in the present invention are generally procaryotic or eucaryotic hosts, including any transformable microorganism in which expression can be achieved. Specifically, host strains may be *Bacillus subtilis, Escherichia coli, Trichoderma reesei* (*longibrachiatum*), *Saccharomyces cerevisiae* or *Aspergillus niger*. Host cells are transformed or transfected with vectors constructed using recombinant DNA techniques. Such transformed host cells are capable of both replicating vectors encoding swollenin and its variants (mutants) or expressing the desired peptide product. In a preferred embodiment according to the present invention, "host cell" means both the cells and protoplasts created from the cells of Trichoderma sp.

"Signal sequence" means a sequence of amino acids bound to the N-terminal portion of a protein which facilitates the secretion of the mature form of the protein outside of the cell. This definition of a signal sequence is a functional one. The mature form of the extracellular protein lacks the signal sequence which is cleaved off during the secretion process.

"DNA construct or vector" (used interchangeably herein) means a nucleotide sequence which comprises one or more DNA fragments or DNA variant fragments encoding any of the novel swollenins or derivatives described above.

"Functionally attached to" means that a regulatory region, such as a promoter, terminator, secretion signal or enhancer region is attached to a structural gene and controls the expression of that gene.

Preparation of Swollenin

The present invention relates to the expression, purification and/or isolation and use of swollenins and derivatives of swollenins. These swollenins are preferably prepared by recombinant methods. However, swollenin proteins for use in the present invention may be obtained by other art recognized means such as purification from natural isolates.

A preferred mode for preparing swollenin according to the present invention comprises transforming a Trichoderma sp. host cell with a DNA construct comprising at least a fragment of DNA encoding a portion or all of the swollenin functionally attached to a promoter. The transformed host cell is then grown under conditions so as to express the desired protein. Subsequently, the desired protein product is purified to substantial homogeneity.

Preferably, the microorganism to be transformed comprises a strain derived from Trichoderma spp. or Aspergillus spp. More preferably, the strain comprises *T. reesei* (*longibrachiatum*) which is useful for obtaining overexpressed protein or *Aspergillus niger* var. *awamori*. For example, RL-P37, described by Sheir-Neiss et al. in *Appl. Microbiol. Biotechnology*, 20 (1984) pp. 46–53 is known to secrete elevated amounts of cellulase enzymes. Functional equivalents of RL-P37 include *Trichoderma reesei* (*longibrachiatum*) strain RUT-C30 (ATCC No. 56765) and strain QM9414 (ATCC No. 26921). Another example includes overproducing mutants as described in Ward et al. in *Appl. Microbiol. Biotechnology* 39:738–743 (1993). It is contemplated that these strains would also be useful in overexpressing Trichoderm spp. swollenin.

Where it is desired to obtain the swollenin protein in the absence of cellulolytic activity, it is useful to obtain, for example, a Trichoderma host cell strain which has had one or more cellulase genes deleted prior to introduction of a DNA construct or plasmid containing the DNA fragment encoding the swollenin. Such strains may be prepared by the method disclosed in U.S. Pat. No. 5,246,853 and WO 92/06209, which disclosures are hereby incorporated by reference. By expressing a swollenin in a host microorganism that is missing one or more cellulase genes, the identification and subsequent purification procedures are simplified. Any gene from Trichoderma sp. which has been cloned can be deleted, for example, the cbh1, cbh2, egl1, and egl3 genes as well as those encoding EGIII and/or EGV protein (see e.g., U.S. Pat. No. 5,475,101 and WO 94/28117, respectively).

Gene deletion may be accomplished by inserting a form of the desired gene to be deleted or disrupted into a plasmid by methods known in the art. The deletion plasmid is then cut at an appropriate restriction enzyme site(s), internal to the desired gene coding region, and the gene coding sequence or part thereof replaced with a selectable marker. Flanking DNA sequences from the locus of the gene to be deleted or disrupted, preferably between about 0.5 to 2.0 kb, remain on either side of the selectable marker gene. An appropriate deletion plasmid will generally have unique restriction enzyme sites present therein to enable the fragment containing the deleted gene, including flanking DNA sequences, and the selectable marker gene to be removed as a single linear piece.

A selectable marker must be chosen so as to enable detection of the transformed fungus. Any selectable marker gene which is expressed in the selected microorganism will be suitable. For example, with Trichoderma sp., the selectable marker is chosen so that the presence of the selectable marker in the transformants will not significantly affect the properties thereof. Such a selectable marker may be a gene which encodes an assayable product. For example, a functional copy of a Trichoderma sp. gene may be used which if lacking in the host strain results in the host strain displaying an auxotrophic phenotype.

In a preferred embodiment, a pyr4$^-$ derivative strain of Trichoderma sp. is transformed with a functional pyr4 gene, which thus provides a selectable marker for transformation. A pyr4$^-$ derivative strain may be obtained by selection of Trichoderma sp. strains which are resistant to fluoroorotic acid (FOA). The pyr4 gene encodes orotidine-5'-monophosphate decarboxylase, an enzyme required for the biosynthesis of uridine. Strains with an intact pyr4 gene grow in a medium lacking uridine but are sensitive to fluoroorotic acid. It is possible to select pyr4$^-$ derivative strains which lack a functional orotidine monophosphate decarboxylase enzyme and require uridine for growth by selecting for FOA resistance. Using the FOA selection technique it is also possible to obtain uridine requiring strains which lack a functional orotate pyrophosphoribosyl transferase. It is possible to transform these cells with a functional copy of the gene encoding this enzyme (Berges and Barreau, 1991, *Curr. Genet.* 19 pp. 359–365). Selection of derivative strains is easily performed using the FOA resistance technique referred to above, and thus, the pyr4 gene is preferably employed as a selectable marker.

To transform pyr4$^-$ Trichoderma sp. so as to be lacking in the ability to express one or more cellulase genes, a single DNA fragment comprising a disrupted or deleted cellulase gene is then isolated from the deletion plasmid and used to transform an appropriate pyr Trichoderma host. Transformants are then identified and selected based on their ability to express the pyr4 gene product and thus compliment the uridine auxotrophy of the host strain. Southern blot analysis is then carried out on the resultant transformants to identify and confirm a double crossover integration event which replaces part or all of the coding region of the genomic copy of the gene to be deleted with the pyr4 selectable markers.

Although the specific plasmid vectors described above relate to preparation of pyr transformants, the present invention is not limited to these vectors. Various genes can be deleted and replaced in the Trichoderma sp. strain using the above techniques. In addition, any available selectable markers can be used, as discussed above. In fact, any Trichoderma sp. gene which has been cloned, and thus identified, can be deleted from the genome using the above-described strategy.

As stated above, the host strains used are derivatives of Trichoderma sp. which lack or have a nonfunctional gene or genes corresponding to the selectable marker chosen. For example, if the selectable marker of pyr4 is chosen, then a specific pyr4$^-$ derivative strain is used as a recipient in the transformation procedure. Similarly, selectable markers comprising Trichoderma sp. genes equivalent to the *Aspergillus nidulans* genes amdS, argB, trpC, niaD may be used. The corresponding recipient strain must therefore be a derivative strain such as argB$^-$, trpC$^-$, niaD$^-$, respectively.

DNA encoding the swollenin protein is then prepared for insertion into an appropriate microorganism. According to the present invention, DNA encoding for a swollenin enzyme comprises all of the DNA necessary to encode for a protein which has functional swollenin activity. Accordingly, DNA may be derived from any microbial source which produces swollenin, provided that the gene may be identified and isolated pursuant to the methods described herein. In a preferred embodiment, the DNA encodes for an swollenin protein derived from Trichoderma sp., and more preferably from *Trichoderma reesei* (*longibrachiatum*).

The DNA fragment or DNA variant fragment encoding the swollenin or derivative may be functionally attached to a fungal promoter sequence, for example, the promoter of the cbh1 or egl1 gene.

It is also contemplated that more than one copy of DNA encoding a swollenid may be recombined into the strain to facilitate overexpression.

The DNA encoding the swollenin may be prepared by the construction of an expression vector carrying the DNA encoding the truncated cellulase. The expression vector carrying the inserted DNA fragment encoding the swollenin may be any vector which is capable of replicating autonomously in a given host organism or of integrating into the DNA of the host, typically a plasmid. In preferred embodiments two types of expression vectors for obtaining expression of genes are contemplated. The first contains DNA sequences in which the promoter, gene coding region, and terminator sequence all originate from the gene to be expressed. Gene truncation may be obtained by deleting away undesired DNA sequences (e.g., coding for unwanted domains) to leave the domain to be expressed under control of its own transcriptional and translational regulatory sequences. A selectable marker is also contained on the vector allowing the selection for integration into the host of multiple copies of the novel gene sequences.

The second type of expression vector is preassembled and contains sequences required for high level transcription and a selectable marker. It is contemplated that the coding region for a gene or part thereof can be inserted into this general purpose expression vector such that it is under the transcriptional control of the expression cassettes promoter and terminator sequences. For example, pTEX is such a general purpose expression vector. Genes or part thereof can be inserted downstream of the strong cbh1 promoter.

In the vector, the DNA sequence encoding the swollenin of the present invention should be operably linked to transcriptional and translational sequences, i.e., a suitable promoter sequence and signal sequence in reading frame to the structural gene. The promoter may be any DNA sequence which shows transcriptional activity in the host cell and may be derived from genes encoding proteins either homologous or heterologous to the host cell. The signal peptide provides for extracellular production of the swollenin or derivatives thereof. The DNA encoding the signal sequence is preferably that which is naturally associated with the gene to be expressed, however the signal sequence from any suitable source, for example an exo-cellobiohydrolases or endoglucanase from Trichoderma, is contemplated in the present invention.

The procedures used to ligate the DNA sequences coding for the swollenins of the present invention with the promoter, and insertion into suitable vectors are well known in the art.

The DNA vector or construct described above may be introduced in the host cell in accordance with known techniques such as transformation, transfection, microinjection, microporation, biolistic bombardment and the like.

In the preferred transformation technique, it must be taken into account that the permeability of the cell wall to DNA in Trichoderma sp. is very low. Accordingly, uptake of the desired DNA sequence, gene or gene fragment is at best minimal. There are a number of methods to increase the permeability of the Trichoderma sp. cell wall in the derivative strain (i.e., lacking a functional gene corresponding to the used selectable marker) prior to the transformation process.

The preferred method in the present invention to prepare Trichoderma sp. for transformation involves the preparation of protoplasts from fungal mycelium. The mycelium can be obtained from germinated vegetative spores. The mycelium is treated with an enzyme which digests the cell wall resulting in protoplasts. The protoplasts are then protected by the presence of an osmotic stabilizer in the suspending medium. These stabilizers include sorbitol, mannitol, potassium chloride, magnesium sulfate and the like. Usually the concentration of these stabilizers varies between 0.8 M to 1.2 M. It is preferable to use about a 1.2 M solution of sorbitol in the suspension medium.

Uptake of the DNA into the host Trichoderma sp. strain is dependent upon the calcium ion concentration. Generally between about 10 mM $CaCl_2$ and 50 mM $CaCl_2$ is used in an uptake solution. Besides the need for the calcium ion in the uptake solution, other items generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). It is believed that the polyethylene glycol acts to fuse the cell membranes thus permitting the contents of the medium to be delivered into the cytoplasm of the Trichoderma sp. strain and the plasmid DNA is transferred to the nucleus. ThFs fusion frequently leaves multiple copies of the plasmid DNA tandemly integrated into the host chromosome.

Usually a suspension containing the Trichoderma sp. protoplasts or cells that have been subjected to a permeability treatment at a density of $10^8$ to $10^9$/ml, preferably $2 \times 10^8$/ml are used in transformation. A volume of 100 microliters of these protoplasts or cells in an appropriate solution (e.g., 1.2 M sorbitol; 50 mM $CaCl_2$) are mixed with the desired DNA. Generally a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation.

Generally, the mixture is then incubated at approximately 0° C. for a period of between 10 to 30 minutes. Additional PEG is then added to the mixture to further enhance the uptake of the desired gene or DNA sequence. The 25% PEG 4000 is generally added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture is then incubated at room temperature before the addition of a sorbitol and $CaCl_2$ solution. The protoplast suspension is then further added to molten aliquots of a growth medium. This growth medium permits the growth of transformants only. Any growth medium can be used in the present invention that is suitable to grow the desired transformants. However, if $Pyr^+$ transformants are being selected it is preferable to use a growth medium that contains no uridine. The subsequent colonies are transferred and purified on a growth medium depleted of uridine.

At this stage, stable transformants may be distinguished from unstable transformants by their faster growth rate and the formation of circular colonies with a smooth, rather than ragged outline on solid culture medium lacking uridine. Additionally, in some cases a further test of stability may made by growing the transformants on solid non-selective medium (i.e. containing uridine), harvesting spores from this culture medium and determining the percentage of these spores which will subsequently germinate and grow on selective medium lacking uridine.

In a particular embodiment of the above method, the swollenins or derivatives thereof are recovered in active form from the host cell after growth in liquid media either as a result of the appropriate post translational processing of the novel swollenin or derivatives thereof.

The expressed swollenins are recovered from the medium by conventional techniques including separations of the cells from the medium by centrifugation, filtration, and precipitation of the proteins in the supernatant or filtrate with a salt, for example, ammonium sulphate. Additionally, chromatography procedures such as ion exchange chromatography or affinity chromatography may be used. Antibodies (polyclonal or monoclonal) may be raised against the natural purified swollenins, or synthetic peptides may be prepared from portions of the swollenin molecule and used to raise polyclonal antibodies.

EXAMPLE 1

*Trichoderma reesei* (*longibrachiatum*) cDNA Clone Encoding a Novel Swollenin

FIGS. 1A–1B show the nucleotile sequence (SEQ ID:NO 1) and predicted corresponding amino acid sequence (SEQ ID:NO 2) of a cDNA done obtained from a library of cDNA prepared from *Trichoderma reesei* (*longibrachietum*) RNA after growth on a mixed carbon source as described by Salocheimo et al. 1994. Molec. Microbiol 13:219–228. The cDNA showed the following characteristics which help to describe the gene:

An open reading frame of 1482 nt was identified and the encoded protein was deduced.

The first 18 amino acids of the predicted protein have the following features expected of a secretion signal sequence and signal cleavage site. There is a positively charged amino acid (lysine) close to the amino-terminal methionine which is followed by a sequence of hydrophobic amino acids and an apparent signal peptidase cleavage site following amino acid Ile18. The predicted N-terminus of the mature swollenin would therefore be Gln-Gln. Similarly, many of the mature cellulases produced by Trichoderma have glutamine at the N-terminus (e.g., CBHI, CBHII, EGI, EGII and EGIII) and both EGI and EGII begin with a pair of glutamine residues reinforcing the conclusion that this is the N-terminus. The mature protein is therefore predicted to be 475 amino acids in length and have a molecular weight of approximately 49.5 kDa, not including any possible glycosylation or other modification, and a calculated pI of approximately 4.6 based on the amino acid composition. There are three potential N-linked glycosylation sites (having the consensus amino acid sequence of N-X-S/T) at Asparagines 160, 336 and 406.

Residues 4 to 39 of the predicted mature protein sequence have close similarity with the cellulose binding domains (CBDs) of cellulases produced by Trichoderma and other fungal cellulases (58% identity with the CBD of CBHII of Trichoderma). CBDs are also associated with some non-cellulolytic extracellular fungal enzymes such as acetyl xylan esterase and mannanase from *Trichoderma reesei* (*longibrachiatum*) and similar identity is shown between swollenin CBD and these CBD's.

Following the CBD of the predicted Trichoderna protein is a region (from residue 41 to approximately residue 86) which is rich in Ser, Thr, Gly and Pro residues and which should share a similar functionality to the linker or hinge regions present in Trichoderma and other fungal cellulases and which connect the CBD with the catalytic domain.

Regions of similarity are observed between the predicted amino acid sequence (SEQ ID NO: 2) of the Trichoderma swollenin of FIGS. 1A–1B and known sequences of higher plant expansins. FIG. 2 shows an alignment between part of the predicted Trichoderme protein and a consensus sequence (SEQ ID NO: 3) derived from nine plant expansins by Shcherban et al., supra. These sequences were aligned using the Jotun Hein algorithm within the Lasergene software package (DNASTAR Inc) and a 36% similarity was calculated between the two amino acid sequences. Of the 322 amino acids of Trichoderma swolenin sequence used in this alignment 70 or 21.7% are identical to the higher plant consensus sequence.

Regions of similarity can also be observed between the *Trichoderma reesei* (*longibrachiatum*) swollenin and human titin protein that is rich in fibronectin type repeats. The homology was detected in a similarity search to the protein sequence databanks carried out with the program BLAST (Altschul et al., 1990, *J. Mol. Biol.* 215:403–410) and the alignments shown as examples have been created by the program. The regions of titin homologous to the *T reesei* swollenin are parts of the fibronectin type repeats. Fibronectin repeats have been found in some bacterial carbohydrate-modifying enzymes (Little et al., 1994, *J. Mol. Evol.* 39:631–643) but not from any fungal protein. A BLAST search reveals no similarity between the plant expansins and fibronectin repeat containing proteins.

| T.r. swo | 283 | GGPYYFALTAVNTNGPGSVTKI | (SEQ. ID NO: 21) |
|---|---|---|---|
| Human titin | 12268 | GNEYYFRVTAVNEYGPGVPTDV | (SEQ. ID NO: 22) |
| T.r. swo | 100 | TKGSVTASWTDPMETLGA | (SEQ. ID NO: 23) |
| Human titin titin | 9114 | TKGSMLVSWTPPLDNGGS | (SEQ. ID NO: 24) |

The *Trichoderma reesei* (*longibrachiatum*) swollenin gene was expressed when the fungus was grown on cellulose as the sole carbon source, but not when grown on glucose as the sole carbon source.

In order to investigate the regulation of swollenin gene expression in Trichoderma the following experiment was performed. *Trichoderma reesei* (*longibrachiatum*) strain QM9414 was grown in shake flasks (28° C., 200 RPM) in a minimal medium (Penttilä et al., 1987, Gene 61:155–164) containing 5% glucose or 2% cellulose for three days. To test for sophorose induction, the strain was grown in a minimal medium with 2% sorbitol for three days and sophorose was added to the final concentration of 1 mM. The culture was continued for another ten hours and the same amount of sophorose was added. The cultivation was ended five hours after the second addition. A 87 h cultivation in 2% sorbitol was carried out without sophorose additions as a control. After the cultivations the mycelium was harvested by filtration with a glass fibre filter, washed with 0.9% NaCl and frozen. Total RNA was isolated from the mycelial samples according to Chirgwin et al. (1979, *Biochem. J.* 18:5294–5299). RNA samples of 5 µg were treated with glyoxal and run in a 1% agarose gel in 10 mM Na-phosphate buffer, pH 7. Capillary blotting onto a Hybond-N nylon membrane (Amersham) was carried out according to manufacturer's instructions. The hybridization probe was prepared by digesting the cDNA library plasmid carrying the swollenin cDNA with EcoRI and Xhol, running the digested plasmid in a 0.8% agarose gel and isolating the cDNA fragment from the gel with the Qiaquick gel extraction kit (Qiagen). The probe was labelled with $^{32}$P-dCTP using the Random Primed DNA labelling kit (Boehringer Mannheim). Hybridization was one for 24 h at 42° C. in 50% formamide, 10% dextran sulphate, 1% SDS, 1 M NaCl, 125 µg/ml herring sperm DNA. The filter was washed at 42° C. in 5×SSPE for 15 minutes, in 1×SSPE, 0.1% SDS for 2×15 minutes and in 0.1×SSPE, 0.1% SDS 2×15 minutes at room temperature. (1×SSPE is 0.18 M NaCl, 1 mM EDTA, 10 mM $NaH_2PO_4$, pH 7.7). The results of this experiment are shown in FIG. 3. No swollenin mRNA was observed after growth on glucose and very little was observed after growth on sorbitol. In contrast, high levels of swollenin mRNA were observed after growth on cellulose or after addition of sophorose to a sorbitol-grown culture.

EXAMPLE 2

Preparation of a Cloned DNA Molecule Encoding Trichoderma Swollenin

The following is provided as a method of preparing a clone comprising an entire swollenin gene described in Example 2. In this example, genomic DNA or cDNA clones derived from Trichoderma and are prepared by using the following procedure.

The oligonucleotides shown below are synthesized:

EXP-A
  5'-GGCGAGATCTTGCTGCCCATCATATTGTGC-3'
  (SEQ ID NO:19)
EXP-B
  5'-GGCGTCTAGACTGCACACCAATGTCAATGT-3' (SEQ ID NO:20)

Oligonuclotide EXP-A contains a BgIII restriction enzyme recognition site near the 5' end followed by the DNA sequence from nt 425 to nt 445 of SEQ ID NO:1. Otigonucleotide EXP-B contains an XbaI recognition site near the 5' end followed by the reverse complement of the DNA sequence from nt 1471 to nt 1490 of SEQ ID NO:1.

Polymerase chain reaction (PCR) was performed using the oligonucleotides EXP-A and EXP-B as primers and total genomic DNA isolated from *Trichoderma reesei* strain QM6a (ATCC 13631) as template. The DNA polymerase enzyme (Pwo polymerase), buffer and deoxynucleotide mixture used were supplied by Boehringer Mannheim. The following conditions were used for PCR; step 1, 1 min. at 94° C.; step 2, 40 sec. at 92° C.; step 3, 1 min. at 50° C., step 4, 2 min. at 72° C. steps 2, 3 and 4 repeated 29 times; step 5, 5 min. at 72° C.

The major DNA product of PCR was a fragment of approximately 1.3 kb as estimated by agarose gel electrophoresis. The PCR product was digested with BglII and XbaI and the 1.3 kb DNA fragment was purified from an agarose electrophoresis gel. This DNA fragment was ligated with pSL1180 (Pharmacia) which had been digested with BglII and XbaI. The resulting plasmid was named pSLexpPCR. DNA sequence analysis confirmed that the 1.3 kb insert in pSLexpPCR corresponded to the expected fragment of the Trichoderma swollenin gene. The DNA sequence revealed the presence of three introns within this 1.3 kb fragment at positions corresponding to between nt 575 and nt 576, between nt 791 and nt 792, and between nt 969 and nt 970 of SEQ ID NO:1.

The plasmid, or the 1.3 kb insert it contains, can now be used as a hybridization probe to allow the entire swollenin gene to be cloned from any genomic DNA or cDNA libraries of interest. The swollenin encoding DNA within the pSLexpPCR does not included the regions corresponding to the CBD or the linker (hinge) region. Therefore, by design, it would be expected to hybridize with other swollenin DNA sequences but not to CBD encoding sequences which may be part of other non-swollenin genes.

Total genomic DNA from *T reesei* (*longibrachiatum*) strain QM6a was digested separately with a variety of different restriction endonucleases and subjected to agarose gel electrophoresis. The DNA was subsequently blotted to a Nytran (S&S) membrane filter and probed with the 1.3 kb BglII-XbaI DNA fragment isolated from pSLexpPCR and labeled with $^{32}P$ by the Megaprime random labeling system supplied by Amersham. Hybridization with the probe was performed at moderate stringency in a buffer containing 30% formamide, 5×SSPE, 0.5% SDS at 38° C. The membrane filter was subsequently washed at moderate stringency in 2×SSC, 0.1% SDS at 55° C. before being exposed to X-ray film. The results indicated that the genomic copy of the *T reesei* swollenin gene resides on an approximately 4.5 kb BgIII fragment, or on an approximately 5.5 kb XbaI fragment.

Given the exemplified swollenin gene as provided above, it would be routine for one of skill in the art to clone the *Trichoderma reesei* swollenin gene from genomic DNA or CDNA libraries by colony hybridization using the PCR fragment inserted in pSLexpPCR as a probe.

EXAMPLE 3

Cloning the Genomic Copy of *T. Reesei* Swollenin and Expression of it in *Aspergmilus niger* var. awamori The genomic copy of *T. reesei* swollenin was cloned by PCR. The template DNA was from *T. reesei* RutC-30 (ATCC 56765) and the primers corresponding to the 5' and 3' ends of the swollenin coding region were designated as GCI-PVS-055 (gcg cag atc tca gca atg gct ggt aag ctt atc ctc g) and GCI-PVS-056 (geg ctc tag atc aat tct ggc taa act gca cac c).

The PCR-amplified fragment was digested with BglII and XbaI and cloned into a BglII-XbaI opened pGAPT-PT resulting in pGAPT-expC. Sequencing the insert revealed that the chromosomal copy of the swollenin gene has five introns.

The chromosomal copy of the swollenin gene (i.e. pGAPT-expC) was transformed into Aspergillus and transformants were screened as described above for the cDNA.

EXAMPLE 4

Method of Isolating DNA Sequences Encoding Swollenins in Microorganisms

The general technique in Examples 2 and 3 may be adapted in conjunction with known techniques to obtain clones comprising swollenin or swollenin-type genes from other fungi and bacteria. Plasmid pSLexpPCR or the isolated 1.3 kb DNA insert encoding part of the swollenin gene (Example 2), may be labelled as can the core region of the swollenin (Example 3). This DNA probe can then be used to hybridize with genomic DNA or cDNA from other fungi or bacteria. Sequences which have been published for higher plant expansins show a very high level of amino acid identity (see, eg., FIGS. 4A–4B, where underlined segments indicate regions of high homology). A comparison of the deduced amino add sequence of the Ticohoderma swollenin with the known amino acid sequences of higher plant expansins identifies certain conserved regions of amino acids between the swollenins and plant expansins. These conserved regions provide the basis for designing degenerate primers for use in PCR amplification of swollenin-encoding DNA from other microorganisms. Such methods are generally known in the art and considered routine (see e.g., McPherson et al., *PCR A Practical Aproach*, pp. 171–186 (1991)). Conserved regions corresponding to amino adds 192–200 and 366–371 of SEQ ID NO:2 are pointed to as being particularly useful for this purpose (see also, highlighted segments of FIG. 2 although other conserved regions could be used.

The sequence at amino add residues 192–200 of SEQ ID NO:2, TSGGACGFG (SEQ. ID NO:14), is highly homologous to the corresponding sequence in the consensus plant expansin sequence TMGGACGYG (SEQ. ID NO. 15) (numbered positions 19–27 in FIGS. 4A–4B). Based on this region of homology, it would be possible to synthesize degenerate oligonucleotides comprising all possible DNA sequences which encode part or all of the amino acid sequence T(M/S)GGACG(Y/F)G (see e.g., McPherson et al., supra, page 174).

The sequence at amino acid residues 366 to 371 of SEQ ID:NO.2, YRRVQC (SEQ. ID NO. 16), is highly homologous to the corresponding sequence in the consensus plant expansin sequences YRRVPC (SEQ ID. NO:17) and FRRVPC (SEQ. ID NO: 18) (numbered positions 127–132 in FIGS. 4A–4B). Based on this region of homology, it would also be possible to synthesize degenerate oligonucleotides to include all possible DNA sequences which encode part or all of the amino acid sequence (F/Y)RRV(P/Q)C. The oligonucleotides derived from this amino acid sequence would be used in conjunction with those derived from the previous mentioned amino acid sequence as primers for routine PCR experiments using genomic DNA. Genomic DNA or cDNA could then easily be obtained from any microbe and used as a template in such PCR experiments. In this way it would be possible to done genes encoding swollenins from a variety of microbes.

EXAMPLE 5

Heterologous Hybridization Method for Isolating Swolienin Encoding Sequences from Other Microorganisms Genomic DNA from different microorganisms was digested with Hind3 and run on 1.0% agarose gel. Gel was depurinated, denatured and blotted, and the membrane was UV-crosslinked as described on page 6. Prehybridization, hybridization, labeling of the probe and detection were done using the DIG/Genius™ System from Boehringer Mannheim.

The probe corresponded to the sequence encoding the core region of *T. reesei* swollenin. The original cDNA subclone (EXAMPLE 1) was digested with Nco1 and Eco1 resulting in a 312 bp DNA fragment which was labeled with DIG-dUTP (dioxigenin-dUTP) via random-primed labeling according to manufacturer's (Boehringer Mannheim) instructions.

The membrane was prehybridized and hybridized in 5×SSC-0.1 % N-lauroylsarcosine-0.02% SDS-1% Genius™ blocking reagent at 45° C. Hybridization (over night) was followed by two 10 minute washes in 6×SSC at room temperature and two 5 minute washes in 6×SSC at 45° C. Detection with an anti-DIG-alkaline phosphatase conjugate and visualization with a chemiluminescence substrate CSPD® were done according to manufacturer's instructions.

Results from this experiment indicated that at least the following species, in addition to *T. reesei*, hybridize to the probe: *Trichoderma koningli*, *Hypocrea lenta* and *Hypocrea schweinitzii*. In this Hind3 digestion *T. reesei* and *T. koningii*, had a over 5 kb band that hybridized with the *T. reesei* swollenin gene. For *H. schweinitzii*, the band that hybridized was 3.7 kb and for *H. lenta* approximately 3.3 kb in size. This method and variations of it (different hybridization and washing conditions) can be used to detect swollenin encoding genes from any organism.

EXAMPLE 6

Preparation of a *Saccharomyces cerevisiae* Clone For Expression of *T. reesei* Swollenin During the course of obtaining the *Trichoderma reesei* cDNA mentioned in Example 1, a *Saccharomyces cerevisiae* clone was obtained which contained an expression plasmid in which the cDNA sequence of SEQ ID NO:1 was inserted between the *S. cerevisiae* PGK1 promoter and the terminator region in plasmid pAJ401 (Saloheimo et al., 1994, *Molec. Microbiol.*, Vol. 13, pp. 219–228 (1994)) according to the method described by Margolles-Clark et al., (*Appl. Environ. Microbiol.*, 62:3840–3846, 1996). Briefly, *T. reesei* cDNA was ligated to the EcoRI-XhoI cut plasmid pAJ401. Plasmid pAJ401 was derived from plasmid pFL60 (Minet and Lacroute, *Curr. Genet.*, Vol. 18, pp. 287–291 (1990) by changing the two cloning sites EcoRI and XhoI between the yeast PGK promoter and terminator into the reverse orientation using specific linkers. Transformation of *E. coli* strain JS4 by electroporation (Bio-Rad) according to the manufacturer's instructions yields a library of 1.3×10$^6$ independent clones. One of these clones contained pAJ401 with the cDNA of SEQ ID NO:1 inserted between the EcoRI and XhoI sites and was subsequently transformed into *S. cerevisiae* strain DBY746. A second yeast clone was obtained which contained pAJ401 without the cDNA sequence of SEQ ID NO:1 for use as a control in Examples 5 and 6.

The two yeast clones, one control clone and one clone containing the *T. reesei* (*longibrachiatum*) swollenin cDNA sequence, were cultured for 2–3 days in fermentors. Either Chemap CMF mini 1 liter or Biolafitte 14 L fermentors were used. The culture medium was synthetic complete medium without uracil (Sherman, 1991, *Methods Enzymol.* 194, 3–21). pH was maintained at 5.0, aeration rate was 1 L/min for the smaller fermentors and 8 L/min for the larger fermentors, and agiyation speed was 300–600 rpm. Following fermentation, the cells were removed by centrifugation and the supernatant was concentrated 50–100 fold.

EXAMPLE 7

Expression of *T. reesei* Swollenin cDNA in *Aspergillus niger* var. *awamori*

Construction of the Aspergillus expression vector

Construction of the Aspergillus expression vector for expression of *T. reesei* swollenin cDNA consisted of three steps: (1) PCR-amplification of the swollenin cDNA and subdoning it into pSP73-hind3 (i.e. HindIII site was killed), (2) exchanging the middle part of the PCR-derived swollenin gene to the original swollenin gene from the cDNA subclone in order to eliminate mistakes derived from PCR-amplification, and (3) subcloning the swollenin-insert into a Aspergillus expression vector pGAPT-PT for expression under the *A. niger* var. *awamori* glaA promoter (glucoamylase).

1. PCR-amplification of the swollenin cDNA: Primers ExAspBgI2 (CATTAGATCTCAGCAATGGCTGGTAAGCTTATCCTC) and ExAspXba1 (CGACTCTAGAAGGATTAGTTCTGGCTAAACTGCACACC) were used for PCR-amplificat ion of the coding regio n of the *T. reesei* swollenin cDNA (vector from example 1).

ExAspBgI2 has a BglII cloning site which is followed by the five last nucleotides of the glaA (glucoamylase) promoter sequence which precede the translation start site (ATG). The ATG in ExAspBgI2 is followed by a 19-mer corresponding to the swollenin signal sequence. ExAspXba1 has a XbaI cloning site, a STOP codon and a sequence which codes for the last 7 codons of the swollenin gene.

The PCR-amplified 1.5 kb swollenin fragment was digested with BglII and XbaI and ligated into BglII-XbaI opened pSP73-Hind3 vector. Before this cloning step pSP73 (Promega) was first deleted for its HindIII site. This was done by opening the vector (pSP73) with HindIII and the protruding ends were filled in with T4 polymerase (with dNTPs), before ligating the vector back together. This vector was designated as pSP73-Hind3.

pSP73-Hind3 containing the 1.5 kb swollenin insert was designated as pPCRAexp.

2. Replacing the PCR-amplified sequence with the original sequence: pPCRAexp was digested with HindIII and BstEII. HindIII cuts the swollenin coding sequence within the signal sequence and BstEII is close to the end of the swollenin coding sequence. The 1.4 kb HindIII-BstEII swollenin fragment from pPCRAexp was discarded and replaced with the 1.4 kb HindIII-BstEII swollenin fragment from the original swollenin cDNA subclone (EXAMPLE 1). The resultant vector was designated as pWTAexp.

3. Cloning into the expression vector: pWTAexp was digested with BglII and XbaI resulting in a 1.5 kb swollenin insert with a complete coding region preceded by five nucleotides of the glaA promoter sequence and flanked by cloning sites enabling ligation between the glaA promoter and terminator sequences in a Aspergillus expression vector pGAPT-PG (described below). The insert and vector sequences were ligated and the resultant vector was designated as pGAPT-exp (6.5 kb). This is the vector for expressing *T. reesei* swollenin cDNA in *A. niger*.

The expression vector pGAPT-PG (5.1 kb) used for construction of pGAPT-exp consists of a 1.1 kb SpeI-BglII fragment of *A. niger* var. *awamori* glaA promoter sequence, 0.2 kb fragment of *A. niger* glaA terminator sequence and 1.6 kb *A. nidulans* pyrG marker gene in pUC18 backbone. The glaA terminator fragment follows the glaA promoter sequence and is separated from it by multiple cloning sites which can be used for inserting sequences to be expressed.

The 3' end of the glaA promoter sequence, i.e. the sequence preceding the translation start site of the swollenin gene in pGAPT-exp has been engineered (multiple cloning sites) and has the following sequence starting from a XmnI site in the glaA promoter:

G M G T G C T T C C T C C C T T T T A G A C G C M C T- G A G A G C C T G A G C T T C A T C C C C A G C AT- CATTAGATCTCAGCMTG in which the ATG in the end is the start codon for the swollenin cDNA.

The surrounding sequence of the STOP codon is following (starting from the 'TAA' stop codon—engineered from the original 'TGA' STOP codon in swollenin):
TAATCCTTCTAGAGTCGACCGCGACGGTGACC
shown up till the BstEII site (GGTGACC) in the glaA terminator sequence.

Transformation of pGAPT-exp to Aspergillus pGAPT-exp was transferred to the strain *A. niger* var. *awamori* dgr246 p2 described in Ward et al. *Appl. Microbiol. Biotechnol.* 39:738–743 (1993). Transformation of Aspergillus follows the same basic procedure as described for Trichoderma on pages 13–15. The transformation procedure of *A. niger* var. *awamori* dgr246 p2 is also described in Ward et al. *Appl. Microbiol. Biotechnol.* 39:738–743 (1993).

Transformants were selected on their ability to grow on minimal nutrients without uridine. The untransformed cells require uridine for growth.

Screening of Transformants

Aspergillus transformants were cultivated in 50 ml liquid medium in 250 ml shake flasks for 5–11 days as described in Ward et al. *Bio/Technology* 8:435–440 (1990). The complex medium contained 15% maltose to induce the glaA promoter and therefore drive expression of the swollenin gene. Culture supernatants were run on SDS-PAGE gels. Aspergillus transformants which were producing the *T. reesei* swollenin had a band running above the 66 kD marker band and this band was missing from lanes of the negative control (Aspergillus strain before the transformation) (FIG. 6).

EXAMPLE 8

Effect of Treatment with *Trichoderma reesei* Swolienin on Cellulose Structure

Whatman No. 3 filter paper circles were cut into strips measuring 2×7 cm. Buffer used was 50 mM sodium acetate, pH 5. The filter paper strips were soaked for at least 30 min. at room temperature in solutions consisting of water, buffer, 8M urea in buffer, or broth produced from yeast cones containing the *T. reesei* swollenin gene or a control yeast clone which does not produce *T. reesei* swollenin in buffer (dilutions ranged from 1 ml of broth in 7 ml buffer to 4 ml broth in 4 ml buffer).

A Thwing-Albert tensile tester was set for a test speed of 0.10 cm/min and tensile energy measured over a range of 0 to 50 lbs. Each strip of filter paper was placed between the clamps and the peak load was measured. The results of this experiment quantify the degree of load that can be held before breaking the paper. Two or three strips were measured for each sample type. The results from several different experiments are given below in Tables 1 and 2.

TABLE 1

| Sample | Trial 1 | Trial 2 | Trial 3 | Average |
| --- | --- | --- | --- | --- |
| buffer | .55 | .58 | .59 | .57 |
| 8M urea | N/A | .36 | .32 | .34 |
| control broth | .49 | .49 | .47 | .48 |
| swo broth | .40 | .42 | .42 | .41 |

TABLE 2

| Sample | Trial 4 | Trial 5 | Average |
| --- | --- | --- | --- |
| buffer | .56 | .59 | .58 |
| 8M urea | .42 | .41 | .42 |
| control 1 ml | .52 | .52 | .52 |
| control 3 ml | .52 | .47 | .50 |
| swo 1 ml | .43 | .42 | .43 |
| swo 3 ml | .46 | .40 | .43 |

As expected, the strips treated with 8M urea, which is known to disrupt hydrogen bonding interactions, cannot hold as high of a load without breaking as strips treated with buffer only. In both experiments, the strips treated with the swollenin broth have a significantly lower maximal load (about 15%) than the strips treated with control broth. The only difference between these two broths is that one is from the fermentation of the yeast strain containing the *T. reesei* swollenin gene, while the control strain does not contain this gene. These results show that there is a component in the swollenin broth which is weakening filter paper.

EXAMPLE 9

Treatment of Cotton Fibers with Swollenin

The yeast clones described above in Example 4 were grown under the conditions specified and the fermentation broth separated from extraneous cell matter and debris. A control clone of yeast, which contained the expression plasmid but without the inserted swollenin encoding cDNA sequence, was also grown under the same conditions and the fermentation broth isolated by removing extraneous cell matter and debris. The culture supernatants from two fermentations, one containing yeast transformed with the swollenin gene and one containing yeast transformed without the swollenin gene as a control, were concentrated approximately 50 fold and were used to determine the effects of incubating *T. reesei* swollenin with cotton fibers. The effects of the two supernatants were further compared with the cellobiohydrolase I (CBHI) for *T. reesei*.

Mercerized cotton fibers were suspended in buffer (50 mM sodium acetate, pH 5.0) containing supernatant from the yeast fermentations (dilution 1:4) and CBHI (dosage 5 $\mu$/g). After incubation for 240 minutes at 25° C., the suspended fibers were filtered off and the amount of reducing sugars released into the filtrates was determined by the method of Sumner and Somers (1944). The fibers were rinsed once with buffer and then suspended in distilled water with glass beads prior to sonication for one minute using a probe tip sonicator (Vibra Cell Sonics and Materials Inc.) The fibers were then stained and visualized by light microscopy to determine gross affects on their structure. The filtrate from the control treatment and the filtrate originating from the yeast strain containing the swollenin gene did not exhibit hydrolytic activity, that is, no reducing sugars were liberated from the cotton fibers. In contrast, CBHI alone liberated reducing sugars 0.08% (of original dry weight). Prior to sonication no difference between fibers treated with supernatant from the control yeast strain versus fibers treated with supernatant from the yeast strain containing the swollenin gene could be discerned. However, after sonication swollen and disorganized regions were apparent in fibers treated with supernatant from the yeast containing the swollenin gene which were not present in the fibers treated with supernatant obtained from the control yeast strain (FIG. 5). CBHI alone caused light fibrillation on the fibers, but no opened and swollen regions, which were typical effects for supernatant from yeast containing the swollenin gene, were detected.

We claim:

1. An isolated swollenin protein obtained from a microbial source, wherein said swollenin protein comprises the amino acid sequence set forth in SEQ ID NO:2.

2. The swollenin protein according to claim 1, wherein said microbial source is a fungus or bacterium.

3. The swollenin protein according to claim 2, wherein said fungus is a filamentous fungus.

4. The swollenin protein according to claim 3, wherein said filamentous fungus is selected the group consisting of Trichoderma species, Humicola species, Neurospora species, Aspergillus species, Fusarium species Penicillum species, and Gliocladium species.

5. The swollenin according to claim 1, wherein said swollenin comprises a sequence having at least 70% sequence identity with the sequence provided in SEQ ID NO:2, wherein said swollenin has the ability to weaken filter paper and/or swell cotton fibers.

6. An animal feed comprising the swollenin of claim 1.

* * * * *

UNITED STATES PATENT AND TRADEMARK OFFICE
CERTIFICATE OF CORRECTION

PATENT NO.    : 6,458,928 B1
DATED         : October 1, 2002
INVENTOR(S)   : Swanson et al.

It is certified that error appears in the above-identified patent and that said Letters Patent is hereby corrected as shown below:

<u>Title page,</u>
Item [73], Assignee, should read -- Genencor --

Signed and Sealed this

Thirtieth Day of December, 2003

JAMES E. ROGAN
*Director of the United States Patent and Trademark Office*

SEQUENCE LISTING (1) GENERAL INFORMATION:

(iii) NUMBER OF SEQUENCES: 31

(2) INFORMATION FOR SEQ ID NO: 1:

(i) SEQUENCE CHARACTERISTICS:
      (A) LENGTH: 1645 base pairs
      (B) TYPE: nucleic acid
      (C) STRANDEDNESS: single
      (D) TOPOLOGY: unknown (ii) MOLECULE TYPE: DNA (genomic)

(ix) FEATURE:
      (A) NAME/KEY: CDS
      (B) LOCATION: 24..1505

(xi) SEQUENCE DESCRIPTION: SEQ ID NO: 1:

```
GGCACGAGGA ACTGTTAGAC GGG ATG GCT GGT AAG CTT ATC CTC GTG GCT         50
                         Met Ala Gly Lys Leu Ile Leu Val Ala
                          1               5

CTA GCA AGC CTT GTA TCA CTC TCT ATT CAG CAG AAT TGC GCA GCA TTA       98
Leu Ala Ser Leu Val Ser Leu Ser Ile Gln Gln Asn Cys Ala Ala Leu
 10              15                  20                  25

TTT GGC CAA TGT GGA GGC ATA GGG TGG TCC GGC ACC ACA TGT TGC GTT      146
Phe Gly Gln Cys Gly Gly Ile Gly Trp Ser Gly Thr Thr Cys Cys Val
                 30                  35                  40

GCT GGC GCC CAG TGC AGT TTT GTC AAT GAC TGG TAC TCC CAG TGC CTT      194
Ala Gly Ala Gln Cys Ser Phe Val Asn Asp Trp Tyr Ser Gln Cys Leu
                     45                  50                  55

GCG TCA ACC GGC GGA AAC CCC CCA AAC GGA ACA ACT TCC TCT AGC TTG      242
Ala Ser Thr Gly Gly Asn Pro Pro Asn Gly Thr Thr Ser Ser Ser Leu
```

-continued

```
              60                       65                       70
GTT TCA CGG ACG TCG TCA GCA TCC TCA TCC GTC GGC TCG TCT TCA CCC       290
Val Ser Arg Thr Ser Ser Ala Ser Ser Ser Val Gly Ser Ser Ser Pro
     75                  80                  85

GGC GGC AAC TCA CCA ACT GGC AGT GCT TCC ACC TAC ACA ACC ACA GAT       338
Gly Gly Asn Ser Pro Thr Gly Ser Ala Ser Thr Tyr Thr Thr Thr Asp
 90                  95                 100                 105

ACA GCT ACC GTG GCT CCT CAT TCG CAG TCT CCT TAC CCC AGC ATT GCC       386
Thr Ala Thr Val Ala Pro His Ser Gln Ser Pro Tyr Pro Ser Ile Ala
                     110                 115                 120

GCA TCC AGT TGC GGA TCG TGG ACC CTC GTG GAT AAT GTT TGC TGC CCA       434
Ala Ser Ser Cys Gly Ser Trp Thr Leu Val Asp Asn Val Cys Cys Pro
             125                 130                 135

TCA TAT TGT GCT AAT GAT GAC ACA TCC GAG TCA TGC TCA GGC TGC GGT       482
Ser Tyr Cys Ala Asn Asp Asp Thr Ser Glu Ser Cys Ser Gly Cys Gly
         140                 145                 150

ACC TGC ACT ACG CCG CCC TCG GCG GAC TGC AAA TCC GGA ACC ATG TAT       530
Thr Cys Thr Thr Pro Pro Ser Ala Asp Cys Lys Ser Gly Thr Met Tyr
     155                 160                 165

CCA GAG GTC CAT CAC GTA TCC AGC AAC GAG AGC TGG CAC TAC AGT AGA       578
Pro Glu Val His His Val Ser Ser Asn Glu Ser Trp His Tyr Ser Arg
170                 175                 180                 185

TCA ACC CAC TTT GGC CTA ACG AGC GGG GCC TGT GGC TTT GGC CTG           626
Ser Thr His Phe Gly Leu Thr Ser Gly Gly Ala Cys Gly Phe Gly Leu
                 190                 195                 200

TAC GGT CTC TGC ACA AAG GGC AGT GTT ACA GCC AGC TGG ACG GAT CCC       674
Tyr Gly Leu Cys Thr Lys Gly Ser Val Thr Ala Ser Trp Thr Asp Pro
             205                 210                 215

ATG CTT GGC GCG ACG TGT GAC GCT TTT TGT ACA GCG TAT CCC CTG CTT       722
Met Leu Gly Ala Thr Cys Asp Ala Phe Cys Thr Ala Tyr Pro Leu Leu
         220                 225                 230

TGC AAA GAC CCT ACC GGC ACT ACC CTT CGT GGC AAC TTC GCA GCT CCA       770
Cys Lys Asp Pro Thr Gly Thr Thr Leu Arg Gly Asn Phe Ala Ala Pro
     235                 240                 245

AAC GGC GAT TAC TAC ACC CAA TTC TGG TCC TCG TTG CCA GGA GCC CTC       818
Asn Gly Asp Tyr Tyr Thr Gln Phe Trp Ser Ser Leu Pro Gly Ala Leu
250                 255                 260                 265

GAT AAC TAC CTG TCC TGC GGC GAG TGC ATT GAG CTG ATA CAA ACA AAG       866
Asp Asn Tyr Leu Ser Cys Gly Glu Cys Ile Glu Leu Ile Gln Thr Lys
                 270                 275                 280

CCC GAT GGG ACC GAT TAT GCT GTC GGA GAA GCC GGC TAC ACG GAT CCA       914
Pro Asp Gly Thr Asp Tyr Ala Val Gly Glu Ala Gly Tyr Thr Asp Pro
             285                 290                 295

ATT ACT CTC GAG ATT GTG GAC AGC TGC CCG TGC AGC GCG AAC TCC AAG       962
Ile Thr Leu Glu Ile Val Asp Ser Cys Pro Cys Ser Ala Asn Ser Lys
         300                 305                 310

TGG TGC TGT GGT CCG GGC GCC GAT CAT TGC GGA GAG ATC GAC TTC AAA      1010
Trp Cys Cys Gly Pro Gly Ala Asp His Cys Gly Glu Ile Asp Phe Lys
     315                 320                 325

TAC GGC TGT CCT CTT CCT GCT GAC AGC ATT CAT CTC GAC CTG TCA GAC      1058
Tyr Gly Cys Pro Leu Pro Ala Asp Ser Ile His Leu Asp Leu Ser Asp
330                 335                 340                 345

ATT GCC ATG GGC CGT TTG CAG GGC AAT GGA TCA CTA ACC AAT GGC GTC      1106
Ile Ala Met Gly Arg Leu Gln Gly Asn Gly Ser Leu Thr Asn Gly Val
                 350                 355                 360

ATC CCG ACT CGA TAT AGA AGA GTC CAA TGC CCC AAA GTT GGG AAC GCC      1154
Ile Pro Thr Arg Tyr Arg Arg Val Gln Cys Pro Lys Val Gly Asn Ala
             365                 370                 375

TAC ATT TGG CTT CGA AAT GGC GGA GGG CCT TAC TAT TTT GCT CTC ACG      1202
Tyr Ile Trp Leu Arg Asn Gly Gly Gly Pro Tyr Tyr Phe Ala Leu Thr
```

```
                Tyr Ile Trp Leu Arg Asn Gly Gly Pro Tyr Tyr Phe Ala Leu Thr
                            380                 385                 390

GCA GTC AAC ACC AAC GGA CCG GGC TCA GTC ACC AAA ATC GAG ATC AAG              1250
Ala Val Asn Thr Asn Gly Pro Gly Ser Val Thr Lys Ile Glu Ile Lys
        395                 400                 405

GGC GCA GAC ACC GAC AAC TGG GTT GCC TTG GTC CAT GAC CCA AAC TAT              1298
Gly Ala Asp Thr Asp Asn Trp Val Ala Leu Val His Asp Pro Asn Tyr
410                 415                 420                 425

ACG AGT AGC CGC CCA CAA GAA CGC TAT GGC AGT TGG GTA ATC CCA CAG              1346
Thr Ser Ser Arg Pro Gln Glu Arg Tyr Gly Ser Trp Val Ile Pro Gln
                430                 435                 440

GGA TCA GGG CCC TTT AAC TTG CCT GTT GGA ATT CGT CTG ACT AGC CCA              1394
Gly Ser Gly Pro Phe Asn Leu Pro Val Gly Ile Arg Leu Thr Ser Pro
            445                 450                 455

ACG GGG GAA CAG ATT GTG AAT GAA CAG GCC ATC AAG ACA TTC ACT CCT              1442
Thr Gly Glu Gln Ile Val Asn Glu Gln Ala Ile Lys Thr Phe Thr Pro
        460                 465                 470

CCG GCC ACA GGT GAC CCC AAT TTT TAC TAC ATT GAC ATT GGT GTG CAG              1490
Pro Ala Thr Gly Asp Pro Asn Phe Tyr Tyr Ile Asp Ile Gly Val Gln
475                 480                 485

TTT AGC CAG AAT TGATGGCAAG CATTGGGCAA TGGGCTTCTT GCTGTGGGAC                  1542
Phe Ser Gln Asn
490

AATGATGTAG GCTAGATTCT CAATGCTTCA AGTATGTGGT GTACGTCTTC GTGTGTATAG            1602

ATAGGTATGC TGTTCACTTA AATACACATC CTTTGGTACG TTG                             1645

(2) INFORMATION FOR SEQ ID NO: 2:

(i) SEQUENCE CHARACTERISTICS:
        (A) LENGTH: 493 amino acids
        (B) TYPE: amino acid
        (D) TOPOLOGY: linear (ii) MOLECULE TYPE: protein (xi) SEQUENCE DESCRIPTION: SEQ ID NO: 2:

Met Ala Gly Lys Leu Ile Leu Val Ala Leu Ala Ser Leu Val Ser Leu
 1               5                  10                  15

Ser Ile Gln Gln Asn Cys Ala Ala Leu Phe Gly Gln Cys Gly Gly Ile
                20                  25                  30

Gly Trp Ser Gly Thr Thr Cys Cys Val Ala Gly Ala Gln Cys Ser Phe
            35                  40                  45

Val Asn Asp Trp Tyr Ser Gln Cys Leu Ala Ser Thr Gly Gly Asn Pro
        50                  55                  60

Pro Asn Gly Thr Thr Ser Ser Leu Val Ser Arg Thr Ser Ser Ala
65                  70                  75                  80

Ser Ser Ser Val Gly Ser Ser Pro Gly Gly Asn Ser Pro Thr Gly
                85                  90                  95

Ser Ala Ser Thr Tyr Thr Thr Asp Thr Ala Thr Val Ala Pro His
                100                 105                 110

Ser Gln Ser Pro Tyr Pro Ser Ile Ala Ala Ser Ser Cys Gly Ser Trp
        115                 120                 125

Thr Leu Val Asp Asn Val Cys Cys Pro Ser Tyr Cys Ala Asn Asp Asp
130                 135                 140

Thr Ser Glu Ser Cys Ser Gly Cys Gly Thr Cys Thr Thr Pro Pro Ser
145                 150                 155                 160

Ala Asp Cys Lys Ser Gly Thr Met Tyr Pro Glu Val His His Val Ser
                165                 170                 175
```

```
Ser Asn Glu Ser Trp His Tyr Ser Arg Ser Thr His Phe Gly Leu Thr
            180                 185                 190

Ser Gly Gly Ala Cys Gly Phe Gly Leu Tyr Gly Leu Cys Thr Lys Gly
        195                 200                 205

Ser Val Thr Ala Ser Trp Thr Asp Pro Met Leu Gly Ala Thr Cys Asp
    210                 215                 220

Ala Phe Cys Thr Ala Tyr Pro Leu Leu Cys Lys Asp Pro Thr Gly Thr
225                 230                 235                 240

Thr Leu Arg Gly Asn Phe Ala Ala Pro Asn Gly Asp Tyr Tyr Thr Gln
                245                 250                 255

Phe Trp Ser Ser Leu Pro Gly Ala Leu Asp Asn Tyr Leu Ser Cys Gly
            260                 265                 270

Glu Cys Ile Glu Leu Ile Gln Thr Lys Pro Asp Gly Thr Asp Tyr Ala
        275                 280                 285

Val Gly Glu Ala Gly Tyr Thr Asp Pro Ile Thr Leu Glu Ile Val Asp
    290                 295                 300

Ser Cys Pro Cys Ser Ala Asn Ser Lys Trp Cys Cys Gly Pro Gly Ala
305                 310                 315                 320

Asp His Cys Gly Glu Ile Asp Phe Lys Tyr Gly Cys Pro Leu Pro Ala
                325                 330                 335

Asp Ser Ile His Leu Asp Leu Ser Asp Ile Ala Met Gly Arg Leu Gln
            340                 345                 350

Gly Asn Gly Ser Leu Thr Asn Gly Val Ile Pro Thr Arg Tyr Arg Arg
        355                 360                 365

Val Gln Cys Pro Lys Val Gly Asn Ala Tyr Ile Trp Leu Arg Asn Gly
    370                 375                 380

Gly Gly Pro Tyr Tyr Phe Ala Leu Thr Ala Val Asn Thr Asn Gly Pro
385                 390                 395                 400

Gly Ser Val Thr Lys Ile Glu Ile Lys Gly Ala Asp Thr Asp Asn Trp
                405                 410                 415

Val Ala Leu Val His Asp Pro Asn Tyr Thr Ser Ser Arg Pro Gln Glu
            420                 425                 430

Arg Tyr Gly Ser Trp Val Ile Pro Gln Gly Ser Gly Pro Phe Asn Leu
        435                 440                 445

Pro Val Gly Ile Arg Leu Thr Ser Pro Thr Gly Glu Gln Ile Val Asn
    450                 455                 460

Glu Gln Ala Ile Lys Thr Phe Pro Pro Ala Thr Gly Asp Pro Asn
465                 470                 475                 480

Phe Tyr Tyr Ile Asp Ile Gly Val Gln Phe Ser Gln Asn
                485                 490

(2) INFORMATION FOR SEQ ID NO: 3:

(i) SEQUENCE CHARACTERISTICS:
        (A) LENGTH: 223 amino acids
        (B) TYPE: amino acid
        (D) TOPOLOGY: unknown (ii) MOLECULE TYPE: protein (xi) SEQUENCE DESCRIPTION: SEQ ID NO: 3:

Gly Gly Trp Gln Ser Ala His Ala Thr Phe Tyr Gly Gly Gly Asp Ala
1               5                   10                  15

Ser Gly Thr Met Gly Gly Ala Cys Gly Tyr Gly Asn Leu Tyr Ser Gln
            20                  25                  30
```

```
Gly Tyr Gly Thr Asn Thr Ala Ala Leu Ser Thr Ala Leu Phe Asn Asn
            35                  40                  45

Gly Leu Ser Cys Gly Ala Cys Phe Glu Leu Thr Cys Asp Asn Asp Pro
        50                  55                  60

Lys Trp Cys Leu Pro Gly Ser Ile Thr Val Thr Ala Thr Asn Phe Cys
65                  70                  75                  80

Pro Pro Asn Phe Ala Leu Pro Asn Asn Asn Gly Gly Trp Cys Asn Pro
                85                  90                  95

Pro Leu Gln His Phe Asp Leu Ala Gln Pro Ala Phe Leu Lys Ile Ala
                100                 105                 110

Gln Tyr Arg Ala Gly Ile Val Pro Val Ala Tyr Arg Val Pro Cys
            115                 120                 125

Lys Lys Arg Gly Gly Ile Arg Phe Thr Ile Asn Gly His Ser Tyr Phe
        130                 135                 140

Asn Leu Val Leu Ile Thr Asn Val Gly Ala Gly Asp Val His Ser
145                 150                 155                 160

Val Ser Ile Lys Gly Ser Arg Thr Gly Trp Gln Ala Met Ser Arg Asn
                165                 170                 175

Trp Gly Gln Asn Trp Gln Ser Asn Ser Tyr Leu Asn Gly Gln Ser Leu
            180                 185                 190

Ser Phe Gln Val Thr Leu Ser Asp Gly Arg Thr Val Thr Ser Asn Val
        195                 200                 205

Ala Pro Ala Asn Trp Gln Phe Gly Gln Thr Phe Gly Gly Gln Phe
    210                 215                 220

(2) INFORMATION FOR SEQ ID NO: 4:

(i) SEQUENCE CHARACTERISTICS:
        (A) LENGTH: 322 amino acids
        (B) TYPE: amino acid
        (D) TOPOLOGY: unknown (ii) MOLECULE TYPE: protein (xi) SEQUENCE DESCRIPTION: SEQ ID NO: 4:

Val His His Val Ser Ser Asn Glu Ser Trp His Tyr Ser Arg Ser Thr
1               5                   10                  15

His Phe Gly Leu Thr Ser Gly Gly Ala Cys Gly Phe Gly Leu Tyr Gly
            20                  25                  30

Leu Cys Thr Lys Gly Ser Val Thr Ala Ser Trp Thr Asp Pro Met Leu
        35                  40                  45

Gly Ala Thr Cys Asp Ala Phe Cys Thr Ala Tyr Pro Leu Leu Cys Lys
    50                  55                  60

Asp Pro Thr Gly Thr Thr Leu Arg Gly Asn Phe Ala Ala Pro Asn Gly
65                  70                  75                  80

Asp Tyr Tyr Thr Gln Phe Trp Ser Ser Leu Pro Gly Ala Leu Asp Asn
                85                  90                  95

Tyr Leu Ser Cys Gly Glu Cys Ile Glu Leu Ile Gln Thr Lys Pro Asp
                100                 105                 110

Gly Thr Asp Tyr Ala Val Gly Glu Ala Gly Tyr Thr Asp Pro Ile Thr
            115                 120                 125

Leu Glu Ile Val Asp Ser Cys Pro Cys Ser Ala Asn Ser Lys Trp Cys
        130                 135                 140

Cys Gly Pro Gly Ala Asp His Cys Gly Glu Ile Asp Phe Lys Tyr Gly
145                 150                 155                 160

Cys Pro Leu Pro Ala Asp Ser Ile His Leu Asp Leu Ser Asp Ile Ala
```

```
                        165                 170                 175
Met Gly Arg Leu Gln Gly Asn Gly Ser Leu Thr Asn Gly Val Ile Pro
                180                 185                 190
Thr Arg Tyr Arg Arg Val Gln Cys Pro Lys Val Gly Asn Ala Tyr Ile
            195                 200                 205
Trp Leu Arg Asn Gly Gly Pro Tyr Tyr Phe Ala Leu Thr Ala Val
210                 215                 220
Asn Thr Asn Gly Pro Gly Ser Val Thr Lys Ile Glu Ile Lys Gly Ala
225                 230                 235                 240
Asp Thr Asp Asn Trp Val Ala Leu Val His Asp Pro Asn Tyr Thr Ser
                245                 250                 255
Ser Arg Pro Gln Glu Arg Tyr Gly Ser Trp Val Ile Pro Gln Gly Ser
            260                 265                 270
Gly Pro Phe Asn Leu Pro Val Gly Ile Arg Leu Thr Ser Pro Thr Gly
        275                 280                 285
Glu Gln Ile Val Asn Glu Gln Ala Ile Lys Thr Phe Thr Pro Pro Ala
            290                 295                 300
Thr Gly Asp Pro Asn Phe Tyr Tyr Ile Asp Ile Gly Val Gln Phe Ser
305                 310                 315                 320
Gln Asn (2) INFORMATION FOR SEQ ID NO: 5:

(i) SEQUENCE CHARACTERISTICS:
        (A) LENGTH: 227 amino acids
        (B) TYPE: amino acid
        (D) TOPOLOGY: unknown (ii) MOLECULE TYPE: protein (xi) SEQUENCE DESCRIPTION: SEQ ID NO: 5:

Asp Tyr Gly Gly Trp Gln Ser Gly His Ala Thr Phe Tyr Gly Gly Gly
1               5                   10                  15
Asp Ala Ser Gly Thr Met Gly Gly Ala Cys Gly Tyr Gly Asn Leu Tyr
                20                  25                  30
Ser Gln Gly Tyr Gly Thr Asn Thr Val Ala Leu Ser Thr Ala Leu Phe
            35                  40                  45
Asn Asn Gly Leu Ser Cys Gly Ala Cys Phe Glu Met Thr Cys Thr Asn
50                  55                  60
Asp Pro Lys Trp Cys Leu Pro Gly Thr Ile Arg Val Thr Ala Thr Asn
65                  70                  75                  80
Phe Cys Pro Pro Asn Phe Ala Leu Pro Asn Asn Asn Gly Gly Trp Cys
                85                  90                  95
Asn Pro Pro Leu Gln His Phe Asp Met Ala Glu Pro Ala Phe Leu Gln
            100                 105                 110
Ile Ala Gln Tyr Arg Ala Gly Ile Val Pro Val Ser Phe Arg Arg Val
        115                 120                 125
Pro Cys Met Lys Lys Gly Gly Val Arg Phe Thr Ile Asn Gly His Ser
            130                 135                 140
Tyr Phe Asn Leu Val Leu Ile Thr Asn Val Gly Gly Ala Gly Asp Val
145                 150                 155                 160
His Ser Val Ser Ile Lys Gly Ser Arg Thr Gly Trp Gln Ser Met Ser
                165                 170                 175
Arg Asn Trp Gly Gln Asn Trp Gln Ser Asn Asn Tyr Leu Asn Gly Gln
            180                 185                 190
```

```
Gly Leu Ser Phe Gln Val Thr Leu Ser Asp Gly Arg Thr Leu Thr Ala
            195                 200                 205

Tyr Asn Leu Val Pro Ser Asn Trp Gln Phe Gly Gln Thr Tyr Glu Gly
            210                 215                 220

Pro Gln Phe
225
```

(2) INFORMATION FOR SEQ ID NO: 6:

(i) SEQUENCE CHARACTERISTICS:
        (A) LENGTH: 234 amino acids
        (B) TYPE: amino acid
        (D) TOPOLOGY: unknown (ii) MOLECULE TYPE: protein (xi) SEQUENCE DESCRIPTION: SEQ ID NO: 6:

```
Phe Thr Ala Ser Gly Trp Ala Pro Ala His Ala Thr Phe Tyr Gly Glu
1               5                   10                  15

Ser Asp Ala Ser Gly Thr Met Gly Gly Ala Cys Gly Tyr Gly Asn Leu
            20                  25                  30

Tyr Gln Thr Gly Tyr Gly Thr Arg Thr Ala Ala Leu Ser Thr Ala Leu
            35                  40                  45

Phe Asn Asp Gly Ala Ser Cys Gly Gln Cys Phe Lys Ile Ile Cys Asp
        50                  55                  60

Tyr Lys Thr Asp Pro Arg Trp Cys Ile Lys Gly Ala Ser Val Thr Ile
65                  70                  75                  80

Thr Ala Thr Asn Phe Cys Pro Pro Asn Tyr Ala Leu Pro Asn Asn Asn
                85                  90                  95

Gly Gly Trp Cys Asn Pro Pro Leu Lys His Phe Asp Met Ala Gln Pro
            100                 105                 110

Ala Trp Gln Lys Ile Gly Ile Tyr Arg Gly Gly Ile Ile Pro Val Leu
            115                 120                 125

Tyr Gln Arg Val Pro Cys Lys Lys Arg Gly Gly Val Arg Phe Thr Val
        130                 135                 140

Asn Gly Arg Asp Tyr Phe Glu Leu Val Leu Ile Thr Asn Val Gly Gly
145                 150                 155                 160

Ala Gly Asp Ile Lys Ser Val Ser Ile Lys Gly Ser Lys Ser Ser Asn
                165                 170                 175

Trp Thr Pro Met Ser Arg Asn Trp Gly Ala Asn Trp Gln Ser Asn Ser
            180                 185                 190

Tyr Leu Asn Gly Gln Ser Leu Ser Phe Lys Val Thr Thr Ser Asp Gly
            195                 200                 205

Gln Val Gln Val Phe Asn Asn Val Val Pro Ser Ser Trp Arg Phe Gly
        210                 215                 220

Gln Thr Phe Ala Ser Lys Val Gln Phe Ser
225                 230
```

(2) INFORMATION FOR SEQ ID NO: 7:

(i) SEQUENCE CHARACTERISTICS:
        (A) LENGTH: 237 amino acids
        (B) TYPE: amino acid
        (D) TOPOLOGY: unknown (xi) SEQUENCE DESCRIPTION: SEQ ID NO: 7:

```
Asn Ser Ala Arg Asp Val Asn Gly Tyr Ala Gly Gly Trp Val Asn
1               5                   10                  15
```

```
Ala His Ala Thr Phe Tyr Gly Gly Asp Ala Ser Gly Thr Met Gly
             20                  25                  30

Gly Ala Cys Gly Tyr Gly Asn Leu Tyr Ser Gln Gly Tyr Gly Thr Asn
             35                  40                  45

Thr Ala Ala Leu Ser Thr Ala Leu Phe Asn Asn Gly Leu Ser Cys Gly
 50                  55                  60

Ala Cys Phe Glu Ile Arg Cys Gln Asn Asp Gly Lys Trp Cys Leu Pro
 65                  70                  75                  80

Gly Ser Ile Val Val Thr Ala Thr Asn Phe Cys Pro Pro Asn Asn Ala
                 85                  90                  95

Leu Pro Asn Asn Ala Gly Gly Trp Cys Asn Pro Gln Gln His Phe
             100                 105                 110

Asp Leu Ser Gln Pro Val Phe Gln Arg Ile Ala Gln Tyr Arg Ala Gly
             115                 120                 125

Ile Val Pro Val Ala Tyr Arg Arg Val Pro Cys Val Arg Arg Gly Gly
 130                 135                 140

Ile Arg Phe Thr Ile Asn Gly His Ser Tyr Phe Asn Leu Val Leu Ile
145                 150                 155                 160

Thr Asn Val Gly Gly Ala Gly Asp Val His Ser Ala Met Val Lys Gly
                 165                 170                 175

Ser Arg Thr Gly Trp Gln Ala Met Ser Arg Asn Trp Gly Gln Asn Trp
             180                 185                 190

Gln Ser Asn Ser Tyr Leu Asn Gly Gln Ser Leu Ser Phe Lys Val Thr
             195                 200                 205

Thr Ser Asp Gly Gln Thr Ile Val Ser Asn Asn Val Ala Asn Ala Gly
             210                 215                 220

Trp Ser Phe Gly Gln Thr Phe Thr Gly Ala Gln Leu Arg
225                 230                 235

(2) INFORMATION FOR SEQ ID NO: 8:

(i) SEQUENCE CHARACTERISTICS:
        (A) LENGTH: 232 amino acids
        (B) TYPE: amino acid
        (D) TOPOLOGY: unknown (ii) MOLECULE TYPE: protein (xi) SEQUENCE DESCRIPTION: SEQ ID NO: 8:

Ile Asn Ser Asp Asp Asn Gly Gly Trp Glu Arg Gly His Ala Thr Phe
 1                   5                  10                  15

Tyr Gly Gly Ala Asp Ala Ser Gly Thr Met Gly Gly Ala Cys Gly Tyr
             20                  25                  30

Gly Asn Leu His Ser Gln Gly Tyr Gly Leu Gln Thr Ala Ala Leu Ser
             35                  40                  45

Thr Ala Leu Phe Asn Ser Gly Gln Lys Cys Gly Ala Cys Phe Glu Leu
 50                  55                  60

Thr Cys Glu Asp Asp Pro Glu Trp Cys Ile Pro Gly Ser Ile Ile Val
 65                  70                  75                  80

Ser Ala Thr Asn Phe Cys Pro Pro Asn Phe Ala Leu Ala Asn Asp Asn
                 85                  90                  95

Gly Gly Trp Cys Asn Pro Pro Leu Lys His Phe Asp Leu Ala Glu Pro
             100                 105                 110

Ala Phe Leu Gln Ile Ala Gln Tyr Arg Ala Gly Ile Val Pro Val Ala
             115                 120                 125

Phe Arg Arg Val Pro Cys Glu Lys Gly Gly Gly Ile Arg Phe Thr Ile
```

```
            130                 135                 140
Asn Gly Asn Pro Tyr Phe Asp Leu Val Leu Ile Thr Asn Val Gly Gly
145                 150                 155                 160

Ala Gly Asp Ile Arg Ala Val Ser Leu Lys Gly Ser Lys Thr Asp Gln
                165                 170                 175

Trp Gln Ser Met Ser Arg Asn Trp Gly Gln Asn Trp Gln Ser Asn Thr
                180                 185                 190

Tyr Leu Arg Gly Gln Ser Leu Ser Phe Gln Val Thr Asp Ser Asp Gly
                195                 200                 205

Arg Thr Val Val Ser Tyr Asp Val Val Pro His Asp Trp Gln Phe Gly
                210                 215                 220

Gln Thr Phe Glu Gly Gly Gln Phe
225                 230

(2) INFORMATION FOR SEQ ID NO: 9:

(i) SEQUENCE CHARACTERISTICS:
        (A) LENGTH: 233 amino acids
        (B) TYPE: amino acid
        (D) TOPOLOGY: unknown (ii) MOLECULE TYPE: protein (xi) SEQUENCE DESCRIPTION: SEQ ID NO: 9:

Gly Tyr Arg Arg Gly Gly His His Pro Gly Gly His Met Gly Pro Trp
1               5                   10                  15

Ile Asn Ala His Ala Thr Phe Tyr Gly Gly Asp Ala Ser Gly Thr
                20                  25                  30

Met Gly Gly Ala Cys Gly Tyr Gly Asn Leu Tyr Ser Gln Gly Tyr Gly
                35                  40                  45

Leu Glu Thr Ala Ala Leu Ser Thr Ala Leu Phe Asp Gln Gly Leu Ser
50                  55                  60

Cys Gly Ala Cys Phe Glu Leu Met Cys Val Asn Asp Pro Gln Trp Cys
65                  70                  75                  80

Ile Lys Gly Arg Ser Ile Val Val Thr Ala Thr Asn Phe Cys Pro Pro
                85                  90                  95

Gly Gly Ala Cys Asp Pro Pro Asn His His Phe Asp Leu Ser Gln Pro
                100                 105                 110

Ile Tyr Glu Lys Ile Ala Leu Tyr Lys Ser Gly Ile Ile Pro Val Met
                115                 120                 125

Tyr Arg Arg Val Arg Cys Lys Arg Ser Gly Gly Ile Arg Phe Thr Ile
                130                 135                 140

Asn Gly His Ser Tyr Phe Asn Leu Val Leu Val Thr Asn Val Gly Gly
145                 150                 155                 160

Ala Gly Asp Val His Ser Val Ser Met Lys Gly Ser Arg Thr Lys Trp
                165                 170                 175

Gln Leu Met Ser Arg Asn Trp Gly Gln Asn Trp Gln Ser Asn Ser Tyr
                180                 185                 190

Leu Asn Gly Gln Ser Leu Ser Phe Val Val Thr Thr Ser Asp Arg Arg
                195                 200                 205

Ser Val Val Ser Phe Asn Val Ala Pro Pro Thr Trp Ser Phe Gly Gln
                210                 215                 220

Thr Tyr Thr Gly Gly Gln Phe Arg Tyr
225                 230

(2) INFORMATION FOR SEQ ID NO: 10:
```

(i) SEQUENCE CHARACTERISTICS:
    (A) LENGTH: 241 amino acids
    (B) TYPE: amino acid
    (D) TOPOLOGY: unknown (ii) MOLECULE TYPE: protein (xi) SEQUENCE DESCRIPTION: SEQ ID NO: 10:

```
Leu Ser Glu Ala Arg Ile Pro Gly Val Tyr Asn Gly Gly Trp Glu
1               5                  10                  15

Thr Ala His Ala Thr Phe Tyr Gly Gly Ser Asp Ala Ser Gly Thr Met
            20                  25                  30

Gly Gly Ala Cys Gly Tyr Gly Asn Leu Tyr Ser Gln Gly Tyr Gly Val
            35                  40                  45

Asn Thr Ala Ala Leu Ser Thr Ala Leu Phe Asn Asn Gly Phe Ser Cys
50                  55                  60

Gly Ala Cys Phe Glu Leu Lys Cys Ala Ser Asp Pro Lys Trp Cys His
65                  70                  75                  80

Ser Gly Ser Pro Ser Ile Phe Ile Thr Ala Thr Asn Phe Cys Pro Pro
            85                  90                  95

Asn Phe Ala Gln Pro Ser Asp Asn Gly Gly Trp Cys Asn Pro Pro Arg
            100                 105                 110

Pro His Phe Asp Leu Ala Met Pro Met Phe Leu Lys Ile Ala Glu Tyr
            115                 120                 125

Arg Ala Gly Ile Val Pro Val Ser Phe Arg Arg Val Pro Cys Arg Lys
130                 135                 140

Arg Gly Gly Ile Arg Phe Thr Ile Asn Gly Phe Arg Tyr Phe Asn Leu
145                 150                 155                 160

Val Leu Val Thr Asn Val Ala Gly Ala Gly Asn Ile Val Arg Leu Gly
            165                 170                 175

Val Lys Gly Thr His Thr Ser Trp Met Thr Met Ser Arg Asn Trp Gly
            180                 185                 190

Gln Asn Trp Gln Ser Asn Ser Val Leu Val Gly Gln Ser Leu Ser Phe
            195                 200                 205

Arg Val Thr Ser Ser Asp Arg Arg Ser Ser Thr Ser Trp Asn Ile Ala
210                 215                 220

Pro Ala Asn Trp Lys Phe Gly Gln Thr Phe Met Gly Lys Asn Phe Arg
225                 230                 235                 240

Val
```

(2) INFORMATION FOR SEQ ID NO: 11:

(i) SEQUENCE CHARACTERISTICS:
        (A) LENGTH: 233 amino acids
        (B) TYPE: amino acid
        (D) TOPOLOGY: unknown (ii) MOLECULE TYPE: protein (xi) SEQUENCE DESCRIPTION: SEQ ID NO: 11:

```
Ala Arg Arg Ala Ala Ala Asp Tyr Gly Ser Trp Gln Ser Ala His Ala
1               5                  10                  15

Thr Phe Tyr Gly Gly Gly Asp Ala Ser Gly Thr Met Gly Gly Ala Cys
            20                  25                  30

Gly Tyr Gly Asn Leu Tyr Ser Thr Gly Tyr Gly Thr Asn Thr Ala Ala
            35                  40                  45

Leu Ser Thr Val Leu Phe Asn Asp Gly Ala Ala Cys Arg Ser Cys Tyr
```

```
                50                  55                  60
Glu Leu Arg Cys Asp Asn Asp Gly Gln Trp Cys Leu Pro Gly Ser Val
 65                  70                  75                  80

Thr Val Thr Ala Thr Asn Leu Cys Pro Pro Asn Tyr Ala Leu Pro Asn
                 85                  90                  95

Asp Asp Gly Gly Trp Cys Asn Pro Pro Arg Pro His Phe Asp Met Ala
            100                 105                 110

Glu Pro Ala Phe Leu Gln Ile Gly Val Tyr Arg Ala Gly Ile Val Pro
            115                 120                 125

Val Ser Tyr Arg Arg Val Pro Cys Val Lys Lys Gly Gly Ile Arg Phe
        130                 135                 140

Thr Ile Asn Gly His Ser Tyr Phe Asn Leu Val Leu Val Thr Asn Val
145                 150                 155                 160

Ala Gly Pro Gly Asp Val Gln Ser Val Ser Ile Lys Gly Ser Ser Thr
                165                 170                 175

Gly Trp Gln Pro Met Ser Arg Asn Trp Gly Gln Asn Trp Gln Ser Asn
            180                 185                 190

Ser Tyr Leu Asp Gly Gln Ser Leu Ser Phe Gln Val Ala Val Ser Asp
        195                 200                 205

Gly Arg Thr Val Thr Ser Asn Asn Val Val Pro Ala Gly Trp Gln Phe
    210                 215                 220

Xaa Gln Thr Phe Glu Gly Gly Gln Phe
225                 230

(2) INFORMATION FOR SEQ ID NO: 12:

(i) SEQUENCE CHARACTERISTICS:
        (A) LENGTH: 233 amino acids
        (B) TYPE: amino acid
        (D) TOPOLOGY: unknown (ii) MOLECULE TYPE: protein (xi) SEQUENCE DESCRIPTION: SEQ ID NO: 12:

Cys Lys Xaa Ser Val Ala Gln Ser Ala Phe Ala Thr Phe Tyr Gly Gly
 1               5                  10                  15

Lys Asp Gly Ser Cys Thr Met Gly Gly Ala Cys Gly Tyr Gly Asn Leu
            20                  25                  30

Tyr Asn Ala Gly Tyr Gly Leu Tyr Asn Ala Ala Leu Ser Ser Ala Leu
         35                  40                  45

Phe Asn Asp Gly Ala Met Cys Gly Ala Cys Tyr Thr Ile Thr Cys Asp
 50                  55                  60

Thr Ser Gln Thr Lys Trp Cys Lys Pro Gly Gly Asn Ser Ile Thr Ile
 65                  70                  75                  80

Thr Ala Thr Asn Leu Cys Pro Pro Asn Trp Ala Leu Pro Ser Asn Ser
                 85                  90                  95

Gly Gly Trp Cys Asn Pro Pro Leu Gln His Phe Asp Met Ser Gln Pro
            100                 105                 110

Ala Trp Glu Asn Ile Ala Val Tyr Gln Ala Gly Ile Val Pro Val Asn
            115                 120                 125

Tyr Lys Arg Val Pro Cys Gln Arg Ser Gly Gly Ile Arg Phe Ala Ile
        130                 135                 140

Ser Gly His Asp Tyr Phe Glu Leu Val Thr Val Thr Asn Val Gly Gly
145                 150                 155                 160

Ser Gly Val Val Ala Gln Met Ser Ile Lys Gly Ser Asn Thr Gly Trp
                165                 170                 175
```

```
Met Ala Met Ser Arg Asn Trp Gly Ala Asn Trp Gln Ser Asn Ala Tyr
            180                 185                 190

Leu Ala Gly Gln Ser Leu Ser Phe Ile Val Gln Leu Asp Asp Gly Arg
        195                 200                 205

Lys Val Thr Ala Trp Asn Val Ala Pro Ser Asn Trp Phe Phe Gly Ala
        210                 215                 220

Thr Tyr Ser Thr Ser Trp Val Gln Phe
225                 230

(2) INFORMATION FOR SEQ ID NO: 13:

(i) SEQUENCE CHARACTERISTICS:
        (A) LENGTH: 258 amino acids
        (B) TYPE: amino acid
        (D) TOPOLOGY: unknown (ii) MOLECULE TYPE: protein (xi) SEQUENCE DESCRIPTION: SEQ ID NO: 13:

Met Ala Ala Ile Leu Leu Leu Thr Ile Ala Ser Leu Thr Ser Leu Phe
1               5                   10                  15

Ala Pro Thr Thr Ala Arg Ile Pro Gly Val Tyr Thr Gly Gly Pro Trp
            20                  25                  30

Thr Ser Ala His Ala Thr Phe Tyr Gly Gly Ser Asp Ala Ser Gly Thr
        35                  40                  45

Met Gly Gly Ala Cys Gly Tyr Gly Asn Leu Tyr Ser Gln Gly Tyr Gly
    50                  55                  60

Val Asn Thr Ala Ala Leu Ser Thr Ala Leu Phe Asn Asn Gly Leu Ser
65                  70                  75                  80

Cys Gly Ala Cys Phe Glu Leu Lys Cys Asp Gln Asp Pro Arg Trp Cys
                85                  90                  95

Asn Pro Gly Asn Pro Ser Ile Leu Ile Thr Ala Thr Asn Phe Cys Pro
            100                 105                 110

Pro Asn Phe Ala Glu Pro Ser Asp Asn Gly Gly Trp Cys Asn Pro Pro
        115                 120                 125

Arg Pro His Phe Asp Leu Ala Met Pro Met Phe Leu Lys Ile Ala Gln
130                 135                 140

Tyr Arg Ala Gly Ile Val Pro Val Ala Tyr Arg Arg Val Pro Cys Arg
145                 150                 155                 160

Lys Ala Gly Gly Ile Arg Phe Thr Ile Asn Gly Phe Arg Tyr Phe Asn
                165                 170                 175

Leu Val Leu Ile Thr Asn Val Ala Gly Ala Gly Asp Ile Val Arg Val
            180                 185                 190

Ser Val Lys Gly Thr Asn Thr Ala Trp Met Thr Met Ser Arg Asn Trp
        195                 200                 205

Gly Gln Asn Trp Gln Ser Asn Ala Val Phe Val Gln Ala Leu Ser
    210                 215                 220

Phe Arg Val Thr Gly Ser Asp Arg Arg Thr Ser Thr Ser Trp Asn Val
225                 230                 235                 240

Ala Pro Pro His Trp Gln Phe Gly Gln Thr Phe Thr Gly Lys Asn Phe
                245                 250                 255

Arg Val (2) INFORMATION FOR SEQ ID NO: 14:

(i) SEQUENCE CHARACTERISTICS:
```

(A) LENGTH: 9 amino acids
        (B) TYPE: amino acid
        (D) TOPOLOGY: unknown (ii) MOLECULE TYPE: protein (xi) SEQUENCE DESCRIPTION: SEQ ID NO: 14:

Thr Ser Gly Gly Ala Cys Gly Phe Gly
1               5

(2) INFORMATION FOR SEQ ID NO: 15:

(i) SEQUENCE CHARACTERISTICS:
        (A) LENGTH: 9 amino acids
        (B) TYPE: amino acid
        (D) TOPOLOGY: unknown (ii) MOLECULE TYPE: protein (xi) SEQUENCE DESCRIPTION: SEQ ID NO: 15:

Thr Met Gly Gly Ala Cys Gly Tyr Gly
1               5

(2) INFORMATION FOR SEQ ID NO: 16:

(i) SEQUENCE CHARACTERISTICS:
        (A) LENGTH: 6 amino acids
        (B) TYPE: amino acid
        (D) TOPOLOGY: unknown (ii) MOLECULE TYPE: protein (xi) SEQUENCE DESCRIPTION: SEQ ID NO: 16:

Tyr Arg Arg Val Gln Cys
1               5

(2) INFORMATION FOR SEQ ID NO: 17:

(i) SEQUENCE CHARACTERISTICS:
        (A) LENGTH: 6 amino acids
        (B) TYPE: amino acid
        (D) TOPOLOGY: unknown (ii) MOLECULE TYPE: protein (xi) SEQUENCE DESCRIPTION: SEQ ID NO: 17:

Tyr Arg Arg Val Pro Cys
1               5

(2) INFORMATION FOR SEQ ID NO: 18:

(i) SEQUENCE CHARACTERISTICS:
        (A) LENGTH: 6 amino acids
        (B) TYPE: amino acid
        (D) TOPOLOGY: unknown (ii) MOLECULE TYPE: protein (xi) SEQUENCE DESCRIPTION: SEQ ID NO: 18:

Phe Arg Arg Val Pro Cys
1               5

(2) INFORMATION FOR SEQ ID NO: 19:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 19:

GGCGAGATCT TGCTGCCCAT CATATTGTGC                                30

(2) INFORMATION FOR SEQ ID NO: 20:

(i) SEQUENCE CHARACTERISTICS:
            (A) LENGTH: 30 base pairs
            (B) TYPE: nucleic acid
            (C) STRANDEDNESS: single
            (D) TOPOLOGY: unknown (ii) MOLECULE TYPE: DNA (genomic)

(xi) SEQUENCE DESCRIPTION: SEQ ID NO: 20:

GGCGTCTAGA CTGCACACCA ATGTCAATGT                                30

(2) INFORMATION FOR SEQ ID NO: 21:

(i) SEQUENCE CHARACTERISTICS:
            (A) LENGTH: 22 amino acids
            (B) TYPE: amino acid
            (D) TOPOLOGY: unknown (ii) MOLECULE TYPE: protein (xi) SEQUENCE DESCRIPTION: SEQ ID NO: 21:

Gly Gly Pro Tyr Tyr Phe Ala Leu Thr Ala Val Asn Thr Asn Gly Pro
1               5                   10                  15

Gly Ser Val Thr Lys Ile
            20

(2) INFORMATION FOR SEQ ID NO: 22:

(i) SEQUENCE CHARACTERISTICS:
            (A) LENGTH: 22 amino acids
            (B) TYPE: amino acid
            (D) TOPOLOGY: unknown (ii) MOLECULE TYPE: protein (xi) SEQUENCE DESCRIPTION: SEQ ID NO: 22:

Gly Asn Glu Tyr Tyr Phe Arg Val Thr Ala Val Asn Glu Tyr Gly Pro
1               5                   10                  15

Gly Val Pro Thr Asp Val
            20

(2) INFORMATION FOR SEQ ID NO: 23:

(i) SEQUENCE CHARACTERISTICS:
            (A) LENGTH: 18 amino acids
            (B) TYPE: amino acid
            (D) TOPOLOGY: unknown (ii) MOLECULE TYPE: protein (xi) SEQUENCE DESCRIPTION: SEQ ID NO: 23:

Thr Lys Gly Ser Val Thr Ala Ser Trp Thr Asp Pro Met Glu Thr Leu
1               5                   10                  15

Gly Ala (2) INFORMATION FOR SEQ ID NO: 24:

(i) SEQUENCE CHARACTERISTICS:

(A) LENGTH: 18 amino acids
        (B) TYPE: amino acid
        (D) TOPOLOGY: unknown (ii) MOLECULE TYPE: protein (xi) SEQUENCE DESCRIPTION: SEQ ID NO: 24:

Thr Lys Gly Ser Met Leu Val Ser Trp Thr Pro Pro Leu Asp Asn Gly
1               5                   10                  15

Gly Ser (2) INFORMATION FOR SEQ ID NO: 25:

(i) SEQUENCE CHARACTERISTICS:
        (A) LENGTH: 58 amino acids
        (B) TYPE: amino acid
        (D) TOPOLOGY: unknown (ii) MOLECULE TYPE: protein (xi) SEQUENCE DESCRIPTION: SEQ ID NO: 25:

Gly Gly Gly Ala Cys Gly Tyr Thr Thr Gly Cys Gly Phe Glu Cys
1               5                   10                  15

Cys Pro His Phe Asp Ala Phe Lys Ala Gly Phe Arg Arg Val Lys Cys
                20                  25                  30

Lys Gly Lys Thr Asn Leu Val Gly Gly Asp Val Val Ile Lys Trp Trp
            35                  40                  45

Gly Trp Gly Glu Gly Thr Thr Pro Trp Tyr
        50                  55

(2) INFORMATION FOR SEQ ID NO: 26:

(i) SEQUENCE CHARACTERISTICS:
        (A) LENGTH: 37 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 26:

GCGCAGATCT CAGCAATGGC TGGTAAGCTT ATCCTCG                                37

(2) INFORMATION FOR SEQ ID NO: 27:

(i) SEQUENCE CHARACTERISTICS:
        (A) LENGTH: 34 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 27:

GCGCTCTAGA TCAATTCTGG CTAAACTGCA CACC                                   34

(2) INFORMATION FOR SEQ ID NO: 28:

(i) SEQUENCE CHARACTERISTICS:
        (A) LENGTH: 36 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 28:

```
CATTAGATCT CAGCAATGGC TGGTAAGCTT ATCCTC                                   36

(2) INFORMATION FOR SEQ ID NO: 29:

(i) SEQUENCE CHARACTERISTICS:
        (A) LENGTH: 38 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 29:

CGACTCTAGA AGGATTAGTT CTGGCTAAAC TGCACACC                                 38

(2) INFORMATION FOR SEQ ID NO: 30:

(i) SEQUENCE CHARACTERISTICS:
        (A) LENGTH: 73 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 30:

GAAGTGCTTC CTCCCTTTTA GACGCAACTG AGAGCCTGAG CTTCATCCCC AGCATCATTA         60

GATCTCAGCA ATG                                                           73

(2) INFORMATION FOR SEQ ID NO: 31:

(i) SEQUENCE CHARACTERISTICS:
        (A) LENGTH: 32 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 31:

TAATCCTTCT AGAGTCGACC GCGACGGTGA CC                                      32
```